US006749857B1

(12) United States Patent
Peters et al.

(10) Patent No.: US 6,749,857 B1
(45) Date of Patent: Jun. 15, 2004

(54) RECOMBINANT DIMERIC ENVELOPE VACCINE AGAINST FLAVIVIRAL INFECTION

(75) Inventors: Iain D. Peters, Bozeman, MT (US); Beth-Ann G. Coller, Woluwe Saint Lambert (BE); Michael McDonell, Bogart, GA (US); John M. Ivy, College Station, TX (US); Kent Harada, Honolulu, HI (US)

(73) Assignee: Hawaii Biotechnology Group, Inc., Aiea, HI (US)

( * ) Notice: Subject to any disclaimer, the term of this patent is extended or adjusted under 35 U.S.C. 154(b) by 0 days.

(21) Appl. No.: 09/376,463

(22) Filed: Aug. 18, 1999

Related U.S. Application Data

(63) Continuation-in-part of application No. 08/904,227, filed on Jul. 31, 1997, now abandoned.
(51) Int. Cl.[7] ................................................. A01J 21/00
(52) U.S. Cl. .................. 424/218.1; 435/69.1; 435/69.7; 530/350; 424/192.1
(58) Field of Search ....................... 530/350; 424/184.1, 424/186.1, 218.1; 422/61

(56) References Cited

U.S. PATENT DOCUMENTS

| 5,494,671 A | 2/1996 | Lai et al. |
| 5,514,375 A | 5/1996 | Paoletti et al. |

FOREIGN PATENT DOCUMENTS

| WO | WO 92/02548 | 2/1992 |
| WO | WO 92/03161 | 3/1992 |

(List continued on next page.)

OTHER PUBLICATIONS

Cardosa, M. J., 1998, "Dengue vaccine design: issues and challenges", Brit. Med. Bull. 54(2):395–405.*
Bancroft, W. H., 1987, "Current status of dengue vaccines and prospects for the future", PRHSJ 6(1):23–26.*

(List continued on next page.)

Primary Examiner—Laurie Scheiner
Assistant Examiner—Jeffrey S. Parkin
(74) Attorney, Agent, or Firm—Morrison & Foerster LLP

(57) ABSTRACT

The present invention discloses and claims vaccines containing, as an active ingredient, a secreted recombinantly produced dimeric form of truncated flaviviral envelope protein. The vaccines are capable of eliciting the production of neutralizing antibodies against flaviviruses. The dimeric forms of truncated flaviviral envelope protein are formed 1) by directly linking two tandem copies of 80% E in a head to tail fashion via a flexible tether; 2) via the formation of a leucine zipper domain through the homodimeric association of two leucine zipper helices each fused to the carboxy terminus of an 80% E molecule; or 3) via the formation of a non-covalently associated four-helix bundle domain formed upon association of two helix-turn-helix moieties each attached to the carboxy terminus of an 80% E molecule. All products are expressed as a polyprotein including prM and the modified 80% E products are secreted from *Drosophila melanogaster* Schneider 2 cells using the human tissue plasminogen activator secretion signal sequence ($tPA_L$). Secreted products are generally more easily purified than those expressed intracellularly, facilitating vaccine production. One embodiment of the present invention is directed to a vaccine for protection of a subject against infection by dengue virus. The vaccine contains, as active ingredient, the dimeric form of truncated envelope protein of a dengue virus serotype. The dimeric truncated E is secreted as a recombinantly produced protein from eucaryotic cells. The vaccine may further contain portions of additional dengue virus serotype dimeric E proteins similarly produced. Another embodiment of the present invention is directed to methods to utilize the dimeric form of truncated dengue envelope protein for diagnosis of infection in individuals at risk for the disease. The diagnostic contains, as active ingredient, the dimeric form of truncated envelope protein of a dengue virus serotype. The dimeric truncated E is secreted as a recombinantly produced protein from eucaryotic cells. The diagnostic may further contain portions of additional dengue virus serotype dimeric E proteins similarly produced.

21 Claims, 15 Drawing Sheets

FOREIGN PATENT DOCUMENTS

| WO | WO 92/03454 | 3/1992 |
|----|-------------|--------|
| WO | WO 96/37221 | 11/1996 |
| WO | WO 97/18311 | 5/1997 |

OTHER PUBLICATIONS

Lai, C. J., et al., 1998, "Evaluation of molecular strategies to develop a live dengue vaccine", Clin. Diag. Virol. 10:173–179.*
Morens, D.M. and S.B. Halstead, 1990, "Measurement of antibody–dependent infection enhancement of four dengue virus serotypes by monoclonal and polyclonal antibodies", J. Gen. Virol. 71(Pt 12):2909–14.*
Kurane, I. and F.E. Ennis, 1992, "Immunity and immunopathology in dengue virus infections", Sem. Immunol. 4 (2):121–7.*
Stephenson, J. R., 1988, "Flavivirus vaccines", Vaccine 6 (6):471–80.*
Harlow, E. et al., (1988) *Antibodies: A Laboratory Manual*, Harlow, et al., eds., Cold Spring Harbor Laboratory, Cold Spring Harbor, New York, pp. 53–137 and 139–243.
Megret, F. et al., (1992) *Virology*, 187:480–491.
Men, R. et al., (1991) *J. Virol*, 65(3):1400–1407.
Walsh, E.E. et al., (1985) *J. Gen. Virol.*, 66:409–415.
Bancroft, W.H. et al., (1987) *PRHSJ*, 6(1):23–26.
Brandt,W.E., (1990) *J. Infect. Disease*, 162:577–583.
Chambers, T.J. et al., (1990) *Ann. Rev. Microbiol.*, 44–649–688.
Culp, J.S. et al., (1991) *Biotechnology*, 9:173–177.
Delenda et al., (1994a) *Arch Virol.*, 139(1–2):197–207.
Delenda et al., (1994b) *J. Gen. Virol.*, 75:1569–1578.
de Oliveira et al., (1994) *Vaccine*, 12(11):1012–1017.
Eckels, K.H. et al., (1993) *Dengue Virus Infections, Control of Virus Diseases, Second Edition*, pp. 343–349.
Hahn, Y.S. et al., (1988) *Virology*, 162:167–180.
Halstead, S.B., (1988) *Science*, 239:476–481.
Henchal, E. A. et al., (1990) *Clin. Microbiol. Rev.*, 3:376–396.
Igarashi, A., (1997) *FEMS Immunol. Med. Microbiol.*, 18:291–300.
Jan, L.R. et al., (1993) *Am. J. Trop. Med. Hyg.*, 48(3):412–423.
Leclerc et al., (1993), *Mol. Immunol.*, 30(7):615–625.
Mandl, C.W. et al., (1989) *J. Virol.*, 63:564–571.
Mason, P.W. et al., (1989) *J. Gen. Virol.*, 70:2037–2049.
Mason, P.W. et al., (1990) *J. Gen. Virol.*, 71:2107–2114.
Monath et al., (1996) *Flaviviruses*, in Fields Virology, Third Edition, Fields et al., eds., Lippincott–Ravin Publishers, Philadelphia, PA, pp. 961–977 and 1002–1004.
Nowak et al., (1987) *Virology*, 156:127–137.
Putnak, R., (1994) *Modern Vaccinology*, 11:231–252.
Rico–Hesse et al., (1998) *Am. J. Trop. Med. Hyg.*, 58(1):96–101.
Roehrig et al., (1992) *Vaccines*, 92:277–281.
Schlesinger et al., (1992) *Biotech.*, 20:289–307.
Srivastava, A.K. et al., (1991) *Microbiol Immunol*, 35:863–870.
Srivastava, A.K. et al., (1990) *Aeta Virol.*, 34:228–238.
Stephenson, J., (1988) *Vaccine*, 6:471–480.
Trirawatanapong, T. et al., (1992) *Gene*, 116:139–150.
Winkler, G. et al., (1987) *J. Gen. Virol.*, 68:2239–2244.
Chambers et al., Vaccine (1997) 15(14):1494–1502.
Heinz et al., Vaccine (1995) 13(17):1636–1642.

* cited by examiner

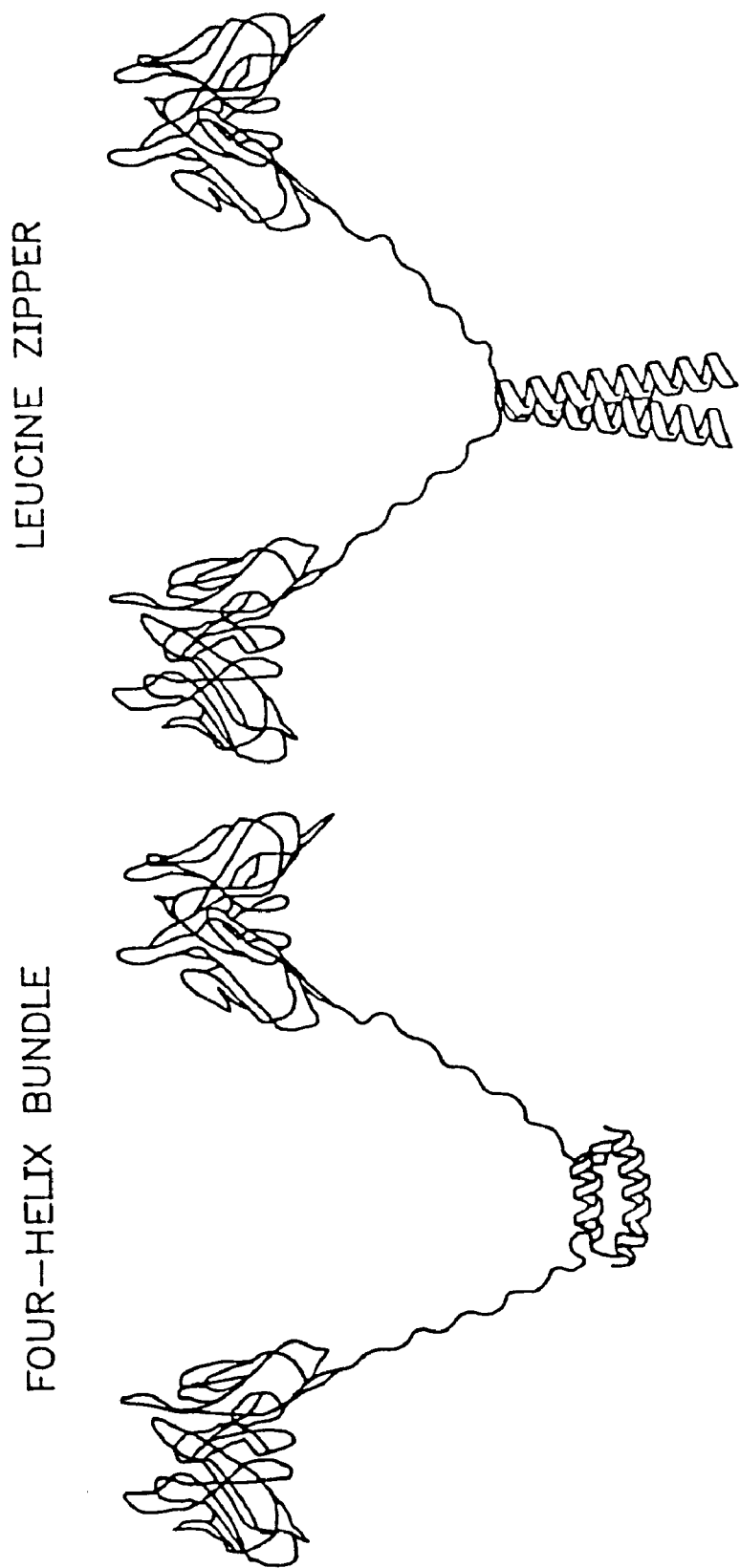
FIG. 2A FOUR-HELIX BUNDLE
FIG. 2B LEUCINE ZIPPER

```
 97                                ATG AATAACCAACG GAAAAAGGCG AGAAACACGC
                                   Met AsnAsnGlnArg LysLysAla ArgAsnThr>
                                   ◆ Capsid 131 CTTTCAATAT GCTGAAACGC GAGAGAAACC GCGTGTCAAC TGTACAACAG TTGACAAAGA
    ProPheAsnMet LeuLysArg GluArgAsn ArgValSerThr ValGlnGln LeuThrLys>

191 GATTCTCACT TGGAATGCTG CAGGGACGAG GACCACTAAA ATTGTTCATG GCCCTGGTGG
    ArgPheSerLeu GlyMetLeu GlnGlyArg GlyProLeuLys LeuPheMet AlaLeuVal>

251 CATTCCTTCG TTTCCTAACA ATCCCACCAA CAGCAGGGAT ATTAAAAAGA TGGGGAACAA
    AlaPheLeuArg PheLeuThr IleProPro ThrAlaGlyIle LeuLysArg TrpGlyThr>

311 TTAAAAAATC AAAGGCTATT AATGTTCTGA GAGGCTTCAG GAAAGAGATT GGAAGGATGC
    IleLysLysSer LysAlaIle AsnValLeu ArgGlyPheArg LysGluIle GlyArgMet>

371 TGAATATCTT AAACAGGAGA CGTAGAACTG CAGGCATGAT CATCATGCTG ATTCCAACAG
    LeuAsnIleLeu AsnArgArg ArgArgThr AlaGlyMetIle IleMetLeu IleProThr>

431 TGATGGCGTT TCATCTGACC ACACGCAACG GAGAACCACA CATGATCGTC AGTAGACAAG
    ValMetAlaPhe HisLeuThr ThrArgAsn GlyGluProHis MetIleVal SerArgGln>
            ◆ PreMembrane 491 AAAAAGGGAA AAGCCTTCTG TTTAAGACAA AGGACGGCAC GAACATGTGT ACCCTCATGG
    GluLysGlyLys SerLeuLeu PheLysThr LysAspGlyThr AsnMetCys ThrLeuMet>

551 CCATGGACCT TGGTGAGTTG TGTGAAGACA CAATCACGTA TAAATGTCCC TTTCTCAAGC
    AlaMetAspLeu GlyGluLeu CysGluAsp ThrIleThrTyr LysCysPro PheLeuLys>

611 AGAACGAACC AGAAGACATA GATTGTTGGT GCAACTCCAC GTCCACATGG GTAACTTATG
    GlnAsnGluPro GluAspIle AspCysTrp CysAsnSerThr SerThrTrp ValThrTyr>

671 GGACATGTAC CACCACAGGA GAGCACAGAA GAGAAAAAAG ATCAGTGGCG CTTGTTCCAC
    GlyThrCysThr ThrThrGly GluHisArg ArgGluLysArg SerValAla LeuValPro>
                                                          ◆ Membrane 731 ACGTGGGAAT GGGATTGGAG ACACGAACTG AAACATGGAT GTCATCAGAA GGGGCCTGGA
    HisValGlyMet GlyLeuGlu ThrArgThr GluThrTrpMet SerSerGlu GlyAlaTrp>

791 AACATGCCCA GAGAATTGAA ACTTGGATTC TGAGACATCC AGGCTTTACC ATAATGGCCG
    LysHisAlaGln ArgIleGlu ThrTrpIle LeuArgHisPro GlyPheThr IleMetAla>

851 CAATCCTGGC ATACACCATA GGAACGACGC ATTTCCAAAG AGTCCTGATA TTCATCCTAC
    AlaIleLeuAla TyrThrIle GlyThrThr HisPheGlnArg ValLeuIle PheIleLeu>

911 TGACAGCCAT CGCTCCTTCA ATGACAATGC GCTGCATAGG AATATCAAAT AGGGACTTTG
    LeuThrAlaIle AlaProSer MetThrMet ArgCysIleGly IleSerAsn ArgAspPhe>
                                        ◆ Envelope 971 TGGAAGGAGT GTCAGGAGGG AGTTGGGTTG ACATAGTTTT AGAACATGGA AGTTGTGTGA
    ValGluGlyVal SerGlyGly SerTrpVal AspIleValLeu GluHisGly SerCysVal>
```

FIG. 3A

```
1031 CGACGATGGC AAAAAATAAA CCAACACTGG ACTTTGAACT GATAAAAACA GAAGCCAAAC
     ThrThrMetAla LysAsnLys  ProThrLeu   AspPheGluLeu IleLysThr  GluAlaLys>

1091 AACCCGCCAC CTTAAGGAAG TACTGTATAG AGGCTAAACT GACCAACACG ACAACAGACT
     GlnProAlaThr LeuArgLys  TyrCysIle   GluAlaLysLeu ThrAsnThr  ThrThrAsp>

1151 CGCGCTGCCC AACACAAGGG GAACCCACCC TGAATGAAGA GCAGGACAAA AGGTTTGTCT
     SerArgCysPro ThrGlnGly  GluProThr   LeuAsnGluGlu GlnAspLys  ArgPheVal>

1211 GCAAACATTC CATGGTAGAC AGAGGATGGG GAAATGGATG TGGATTATTT GGAAAAGGAG
     CysLysHisSer MetValAsp  ArgGlyTrp   GlyAsnGlyCys GlyLeuPhe  GlyLysGly>

1271 GCATCGTGAC CTGTGCCATG TTCACATGCA AAAAGAACAT GGAGGGAAAA ATTGTGCAGC
     GlyIleValThr CysAlaMet  PheThrCys   LysLysAsnMet GluGlyLys  IleValGln>

1331 CAGAAAACCT GGAATACACT GTCGTTATAA CACCTCATTC AGGGGAAGAA CATGCAGTCG
     ProGluAsnLeu GluTyrThr  ValValIle   ThrProHisSer GlyGluGlu  HisAlaVal>

1391 GAAATGACAC AGGAAAACAT GGTAAAGAAG TCAAGATAAC ACCACAGAGC TCCATCACAG
     GlyAsnAspThr GlyLysHis  GlyLysGlu   ValLysIleThr ProGlnSer  SerIleThr>

1451 AGGCGGAACT GACAGGCTAT GGCACTGTTA CGATGGAGTG CTCTCCAAGA ACGGGCCTCG
     GluAlaGluLeu ThrGlyTyr  GlyThrVal   ThrMetGluCys SerProArg  ThrGlyLeu>

1511 ACTTCAATGA GATGGTGTTG CTGCAAATGA AAGACAAAGC TTGGCTGGTG CACAGACAAT
     AspPheAsnGlu MetValLeu  LeuGlnMet   LysAspLysAla TrpLeuVal  HisArgGln>

1571 GGTTCCTAGA CCTACCGTTG CCATGGCTGC CCGGAGCAGA CACACAAGGA TCAAATTGGA
     TrpPheLeuAsp LeuProLeu  ProTrpLeu   ProGlyAlaAsp ThrGlnGly  SerAsnTrp>

1631 TACAGAAAGA GACACTGGTC ACCTTCAAAA ATCCCCATGC GAAAAAACAG GATGTTGTTG
     IleGlnLysGlu ThrLeuVal  ThrPheLys   AsnProHisAla LysLysGln  AspValVal>

1691 TCTTAGGATC CCAAGAGGGG GCCATGCATA CAGCACTCAC AGGGGCTACG GAAATCCAGA
     ValLeuGlySer GlnGluGly  AlaMetHis   ThrAlaLeuThr GlyAlaThr  GluIleGln>

1751 TGTCATCAGG AAACCTGCTG TTCACAGGAC ATCTTAAGTG CAGGCTGAGA ATGGACAAAT
     MetSerSerGly AsnLeuLeu  PheThrGly   HisLeuLysCys ArgLeuArg  MetAspLys>

1811 TACAACTTAA AGGGATGTCA TACTCCATGT GCACAGGAAA GTTTAAAGTT GTGAAGGAAA
     LeuGlnLeuLys GlyMetSer  TyrSerMet   CysThrGlyLys PheLysVal  ValLysGlu>

1871 TAGCAGAAAC ACAACATGGA ACAATAGTCA TTAGAGTACA ATATGAAGGA GACGGCTCTC
     IleAlaGluThr GlnHisGly  ThrIleVal   IleArgValGln TyrGluGly  AspGlySer>
                *
1931 CATGCAAGAT CCCTTTTGAG ATAATGGATC TGGAAAAAAG ACATGTTTTG GGCCGCCTGA
     ProCysLysIle ProPheGlu  IleMetAsp   LeuGluLysArg HisValLeu  GlyArgLeu>
        *                       *
1991 TCACAGTCAA CCCAATTGTA ACAGAAAAGG ACAGCCCAGT CAACATAGAA GCAGAACCTC
     IleThrValAsn ProIleVal  ThrGluLys   AspSerProVal AsnIleGlu  AlaGluPro>

2051 CATTCGGAGA CAGCTACATC ATCATAGGAG TGGAACCAGG ACAATTGAAG CTGGACTGGT
     ProPheGlyAsp SerTyrIle  IleIleGly   ValGluProGly GlnLeuLys  LeuAspTrp>
```

FIG. 3B

2111 TCAAGAAAGG AAGTTCCATC GGCCAAATGT TTGAGACAAC AATGAGGGGA GCGAAAAGAA
     PheLysLysGly SerSerIle GlyGlnMet PheGluThrThr MetArgGly AlaLysArg>

2171 TGGCCATTTT GGGCGACACA GCCTGGGATT TTGGATCTCT GGGAGGAGTG TTCACATCAA
     MetAlaIleLeu GlyAspThr AlaTrpAsp PheGlySerLeu GlyGlyVal PheThrSer>

2231 TAGGAAAGGC TCTCCACCAG GTTTTTGGAG CAATCTACGG GGCTGCTTTC AGTGGGGTCT
     IleGlyLysAla LeuHisGln ValPheGly AlaIleTyrGly AlaAlaPhe SerGlyVal>

2291 CATGGACTAT GAAGATCCTC ATAGGAGTTA TCATCACATG GATAGGAATG AACTCACGTA
     SerTrpThrMet LysIleLeu IleGlyVal IleIleThrTrp IleGlyMet AsnSerArg>

2351 GCACATCACT GTCTGTGTCA CTGGTATTAG TGGGAATCGT GACACTGTAC TTGGGAGTTA
     SerThrSerLeu SerValSer LeuValLeu ValGlyIleVal ThrLeuTyr LeuGlyVal>

2411 TGGTGCAGGC CGATAGTGGT TGCGTTGTGA GCTGGAAGAA CAAAGAACTA AAATGTGGCA
     MetValGlnAla AspSerGly CysValVal SerTrpLysAsn LysGluLeu LysCysGly>
     ◆ NS1

2471 GTGGAATATT CGTCACAGAT AACGTGCATA CATGGACAGA ACAATACAAG TTCCAACCAG
     SerGlyIlePhe ValThrAsp AsnValHis ThrTrpThrGlu GlnTyrLys PheGlnPro>

2531 AATCCCCTTC AAAACTGGCT TCAGCCATCC AGAAAGCTCA TGAAGAGGGC ATCTGTGGAA
     GluSerProSer LysLeuAla SerAlaIle GlnLysAlaHis GluGluGly IleCysGly>

2591 TCCGCTCAGT AACAAGACTG GAAAATCTTA TGTGGAAACA AATAACATCA GAATTGAATC
     IleArgSerVal ThrArgLeu GluAsnLeu MetTrpLysGln IleThrSer GluLeuAsn>

2651 ATATTCTATC AGAAAATGAA GTGAAACTGA CCATCATGAC AGGAGACATC AAAGGAATCA
     HisIleLeuSer GluAsnGlu ValLysLeu ThrIleMetThr GlyAspIle LysGlyIle>

2711 TGCAGGTAGG AAAACGATCT CTGCGGCCTC AACCCACTGA GTTGAGGTAT TCATGGAAAA
     MetGlnValGly LysArgSer LeuArgPro GlnProThrGlu LeuArgTyr SerTrpLys>

2771 CATGGGGTAA AGCGAAAATG CTCTCCACAG AACTCCATAA TCAGACCTTC CTCATTGATG
     ThrTrpGlyLys AlaLysMet LeuSerThr GluLeuHisAsn GlnThrPhe LeuIleAsp>

2831 GTCCCGAAAC AGCAGAATGC CCCAACACAA ACAGAGCTTG GAATTCACTA GAAGTTGAGG
     GlyProGluThr AlaGluCys ProAsnThr AsnArgAlaTrp AsnSerLeu GluValGlu>

2891 ACTACGGCTT TGGAGTATTC ACTACCAATA TATGGCTAAG ATTGAGAGAA AAGCAGGATG
     AspTyrGlyPhe GlyValPhe ThrThrAsn IleTrpLeuArg LeuArgGlu LysGlnAsp>

2951 CATTTTGTGA CTCAAAACTC ATGTCAGCGG CCATAAAGGA CAACAGAGCC GTCCATGCTG
     AlaPheCysAsp SerLysLeu MetSerAla AlaIleLysAsp AsnArgAla ValHisAla>

3011 ATATGGGTTA TTGGATAGAA AGCGCACTCA ATGATACATG GAAGATAGAG AAAGCTTCTT
     AspMetGlyTyr TrpIleGlu SerAlaLeu AsnAspThrTrp LysIleGlu LysAlaSer>

3071 TCATTGAAGT CAAAAGTTGC CACTGGCCAA AGTCACACAC TCTATGGAGT AATGGAGTGC
     PheIleGluVal LysSerCys HisTrpPro LysSerHisThr LeuTrpSer AsnGlyVal>

3131 TAGAAAGCGA GATGGTAATT CCAAAGAATT TCGCTGGACC AGTGTCACAA CATAATAACA
     LeuGluSerGlu MetValIle ProLysAsn PheAlaGlyPro ValSerGln HisAsnAsn>

FIG. 3C

```
3191  GACCAGGCTA  TCACACACAA  ACAGCAGGAC  CTTGGCATCT  AGGCAAGCTT  GAGATGGACT
      ArgProGlyTyr HisThrGln  ThrAlaGly   ProTrpHisLeu GlyLysLeu  GluMetAsp>

3251  TTGATTTCTG  CGAAGGGACT  ACAGTGGTGG  TAACCGAGGA  CTGTGGAAAC  AGAGGGCCCT
      PheAspPheCys GluGlyThr  ThrValVal   ValThrGluAsp CysGlyAsn  ArgGlyPro>

3311  CTTTAAGAAC  AACCACTGCC  TCAGGAAAAC  TCATAACGGA  ATGGTGTTGT  CGATCTTGCA
      SerLeuArgThr ThrThrAla  SerGlyLys   LeuIleThrGlu TrpCysCys  ArgSerCys>

3371  CACTACCACC  ACTAAGATAC  AGAGGTGAGG  ATGGATGCTG  GTACGGGATG  GAAATCAGAC
      ThrLeuProPro LeuArgTyr  ArgGlyGlu   AspGlyCysTrp TyrGlyMet  GluIleArg>

3431  CATTGAAAGA  GAAAGAAGAA  AATCTGGTCA  GTTCTCTGGT  CACAGCC
      ProLeuLysGlu LysGluGlu  AsnLeuVal   SerSerLeuVal ThrAla
```

RECOMBINANT DIMERIC ENVELOPE VACCINE AGAINST FLAVIVIRAL INFECTION

This is a continuation-in-part of application Ser. No. 08/904,227, filed Jul. 31, 1997, now abandoned which is incorporated herein in its entirety.

TECHNICAL FIELD

This invention relates to protection against and diagnosis of flaviviral infection. More specifically, the invention concerns recombinantly produced dimers of truncated flaviviral envelope protein secreted as mature proteins from eucaryotic cells and which induce high titer virus neutralizing antibodies believed to be important in protection against flaviviral infection and which are useful in diagnosis of infection by the virus.

BACKGROUND ART

The four serotypes of dengue virus (DEN-1, DEN-2, DEN-3, and DEN-4) belong to the family Flaviviridae which also includes the Japanese encephalitis virus (JE), Tick-borne encephalitis virus (TBE), West Nile virus (WN), and the family prototype, Yellow fever virus (YF). Flaviviruses are small, enveloped viruses containing a single, positive-strand, genomic RNA. The envelope of flaviviruses is derived from the host cell membrane and is decorated with virally-encoded transmembrane proteins membrane (M) and envelope (E). While mature E protein and the precursor to M, prM, are glycosylated, the much smaller mature M protein is not. The E glycoprotein, which is the largest viral structural protein, contains functional domains responsible for cell surface attachment and intraendosomal fusion activities. It is also a major target of the host immune system, inducing virus neutralizing antibodies, protective immunity, as well as antibodies which inhibit hemagglutination.

Dengue viruses are transmitted to man by mosquitoes of the genus Aedes, primarily *A. aegypti* and *A. albopictus*. The viruses cause an illness manifested by high fever, headache, aching muscles and joints, and rash. Some cases, typically in children, result in a more severe forms of infection, dengue hemorrhagic fever and dengue shock syndrome (DHF/DSS), marked by severe hemorrhage, vascular permeability, or both, leading to shock. Without diagnosis and prompt medical intervention, the sudden onset and rapid progression of DHF/DSS can be fatal.

Flaviviruses are the most significant group of arthropod-transmitted viruses in terms of global morbidity and mortality with an estimated one hundred million cases of dengue fever occurring annually (Halstead, 1988). With the global increase in population and urbanization especially throughout the tropics, and the lack of sustained mosquito control measures, the mosquito vectors of flavivirus have distributed throughout the tropics, subtropics, and some temperate areas, bringing the risk of flaviviral infection to over half the world's population. Modern jet travel and human emigration have facilitated global distribution of dengue serotypes, such that now multiple serotypes of dengue are endemic in many regions. Accompanying this in the last 15 years has been an increase in the frequency of dengue epidemics and the incidence of DHF/DSS. For example, in Southeast Asia, DHF/DSS is a leading cause of hospitalization and death among children (Hayes and Gubler, 1992).

The flaviviral genome is a single strand, positive-sense RNA molecule, approximately 10,500 nucleotides in length containing short 5' and 3' untranslated regions, a single long open reading frame, a 5' cap, and a nonpolyadenylated 3' terminus. The complete nucleotide sequence of numerous flaviviral genomes, including all four DEN serotypes and YF virus have been reported (Fu et al., 1992; Deubel et al, 1986; Hahn et al, 1988; Osatomi et al., 1990; Zhao et al, 1986; Mackow et al., 1987; Rice et al., 1985). The ten gene products encoded by the single open reading frame are translated as a polyprotein organized in the order, capsid (C), premembrane/membrane (prM/M), envelope (E), nonstructural protein (NS) 1, NS2a, NS2b, NS3, NS4a, NS4b, and NS5 (Chambers, et al. 1990). Processing of the encoded polyprotein is initiated cotranslationally, and full maturation requires both host and virally-encoded proteases. The sites of proteolytic cleavage in the YF virus have been determined by comparing the nucleotide sequence and the amino terminal sequences of the viral proteins. Subsequent to initial processing of the polyprotein, prM is converted to M during viral release (Wengler, G. et al., *J Virol* (1989) 63:2521–2526) and anchored C is processed during virus maturation (Nowak et al., *Virology* (1987) 156:127–137).

While all dengue viruses are antigenically related, antigenic distinctions exist which define the four dengue virus serotypes. Infection of an individual with one serotype does not apparently provide long-term immunity against the other serotypes. In fact, secondary infections with heterologous serotypes are becoming increasingly prevalent as multiple serotypes co-circulate in a geographic area. In general, primary infections elicit mostly IgM antibodies directed against type-specific determinants. On the other hand, secondary infection by a heterologous serotype is characterized by IgG antibodies that are flavivirus crossreactive. Dengue virus vaccine development is complicated by the observation that immunity acquired by infection with one serotype may in fact enhance pathogenicity by dengue virus of other types. Halstead (1982) demonstrated that anti-dengue antibodies can augment virus infectivity in vitro, and proposes that serotype crossreactive, non-neutralizing antibodies to E enhance infection in vivo, resulting in DHF/DSS (Halstead, 1981). This viewpoint is not however, universally accepted (Rosen, 1989). For example, Kurane et al (1991) proposed that dengue serotype-cross-reactive $CD4^+$ $CD8^-$ cytotoxic T cells (CTLs) specific for NS3 may contribute to the pathogenesis of DHF/DSS by producing IFN-$\gamma$ and by lysing dengue virus-infected monocytes. Recent evidence demonstrating that CTLs specific for E are not serotype-crossreactive may suggest that use of E subunit vaccines would not induce the potentially harmful cross-reactive CTL response (Livingston et al, 1994). Regardless of the mechanism for enhanced pathogenicity of a secondary, heterologous dengue viral infection, strategies employing a tetravalent vaccine should avoid such complications. Helpful reviews of the nature of the flaviviral diseases, the history of attempts to develop suitable vaccines, and structural features of flaviviruses in general as well as the molecular structural features of the envelope protein of flaviviruses are available (Halstead 1988; Brandt 1990; Chambers et al., 1990; Mandl et al., 1989; Henchal and Putnak, 1990; Putnak 1994; Rey et al., 1995).

Although many approaches to dengue virus vaccines have been pursued, there is no acceptable vaccine currently available. Until recently, the low titer of dengue virus grown in culture has made a killed vaccine impractical, and candidate live-attenuated dengue virus vaccine strains tested to date have proven unsatisfactory (see, e.g., Eckels et al, 1984; Bancroft et al, 1984; McKee et al, 1987), although live attenuated candidate vaccine strains continue to be developed and tested (Hoke et al, 1990; Bhamarapravati et al, 1987). The construction of several full-length infectious flavivirus clones (Rice et al., 1989; Lai et al., 1991; Sumiyoshi et al., 1992) has facilitated studies aimed at identifying the determinants of virulence in flaviviruses (Bray and Lai, 1991; Chen et al., 1995; Kawano et al., 1993). However, these studies are in preliminary stages and little information on virulence has been obtained. A similar approach to vaccine development in the poliovirus system, while extremely informative, has taken years.

In the absence of effective live attenuated or killed flavivirus vaccines, a significant effort has been invested in the development of recombinant, flaviviral subunit or viral-vectored vaccines. Many of the vaccine efforts which use a recombinant DNA approach have focused on the E glycoprotein. This glycoprotein is a logical choice for a subunit vaccine as it is exposed on the surface of the virus and is believed to be responsible for eliciting protective immunity as monoclonal antibodies directed against purified flaviviral E proteins are neutralizing in vitro and some have been shown to confer passive protection in vivo (Henchal et al., 1985; Heinz et al., 1983; Mathews et al., 1984; Hawkes et al., 1988; Kimuro-Kuroda and Yasui, 1988).

Although the primary amino acid sequence of flaviviral E glycoproteins are variable (45–80% identity), all have twelve conserved cysteine residues, forming six disulfide bridges, and nearly superimposable hydrophilicity profiles suggesting that they probably have similar secondary and tertiary structures. Recently, the structure of a soluble fragment of the tick-borne encephalitis (TBE) virus envelope glycoprotein was solved at 2 Å resolution (Rey et al., 1995). This analysis demonstrated that the envelope glycoprotein in its native form is a homodimer which presumably extends parallel to the virion surface. This dimer is formed by an anti-parallel association of the two envelope glycoproteins stabilized by polar interactions along the central region of the dimer, and by non-polar interactions at either end (FIG. 1). The dimer is slightly curved relative to the virion surface, perhaps conforming to the shape of the lipid envelope. The convex, external face contains the major immunogenic sites and the carbohydrate side chains. The carboxy terminus extends from the concave internal face down toward the membrane. Based upon sequence alignments and conservation of cysteine residues involved in disulfide bridges, the authors suggest that the TBE structure serves as a good model for all flavivirus envelopes. Therefore, recombinant soluble dengue E expressed as a dimer might induce a more potent antiviral response than monomeric E because it more closely resembles the natural envelope glycoprotein.

Recombinant flavivirus E glycoprotein has been expressed in several systems to date (See Putnak, 1994 for recent review). In general the systems have proven unsatisfactory for production of a cost-effective flavivirus vaccine due to limitations in antigen quality, quantity, or both. The following paragraphs highlight the major flavivirus vaccine efforts and summarize the results obtained to date.

Bioenvelope glycoproteins vary widely in primary, secondary, tertiary, and quaternary structure. Functional similarity does not necessarily imply structural similarity. To demonstrate the type of variation seen in viral envelope glycoproteins one need look no further than the structures of HIV envelope, Tick Borne Encephalitis (TBE) virus envelope (a flavivirus very similar to dengue), influenza virus hemagglutinin glycoprotein, and Semliki Forest Virus envelope (SFV; an alpha virus). In terms of primary structure, the envelope glycoproteins tend to be the most highly divergent of any viral gene and thus minimal sequence similarity exists even within groups of closely related viruses. As one looks at highly divergent viruses (e.g. HIV and TBE or dengue) the sequence similarity is almost non-existent. In addition, they vary significantly in terms of secondary, tertiary, and quaternary structure as well. As illustrated in Kwong, P. D. et al. Nature (1998) 393:648–659, the structure of the HIV gp120 envelope glycoprotein is quite globular in nature and in fact does not include a transmembrane domain. The membrane anchor function of the HIV envelpe glycoprotein is provided by another protein, gp41 which associates non-covalently as a heterodimer with the gp120 protein maintaining its association with the membrane. In contrast, the structure of the flavivirus TBE envelope glycoprotein (Rey, F. A. et al. Nature (1995) 375:291–298) demonstrated that it exhibits an elongated structure. However, in contrast to other viral envelope glycoproteins which also have an elongated structure (e.g. influenza virus hemagglutinin discussed below) the elongated structure lies parallel to the membrane in a rather flat presentation. In fact, the flavivirus envelope exists on the surface of the membrane as a homodimer with head to tail orientation of the two monomers and is anchored in the membrane by its own transmembrane domain. The structure of the envelope glycoproteins of influenza virus (hemagglutinin and neuraminidase), while also elongated in form, exist as spikes protruding from the membrane and include unique structural features such as a hinge region (Reviewed in Fields, B. N. and D. M. Knipe (eds.) *Virology, 2$^{nd}$ ed.*, Raven Press, NY, 1990). The hemagglutinin spikes are formed by the association of three monomers in a triple-stranded coiled-coil structure markedly different from the head to tail dimer form of the TBE envelope. Finally, although the alphaviruses are relatively closely related to the flaviviruses, the structure of an alphavirus envelope glycoprotein also varies significantly from the structure described for flaviviruses (Helenius, A. Cell (1995) 81:651–653). The SFV envelope glycoproteins have been shown to form spikes which project 80 nm from the membrane surface and consist of three E1–E2 pairs. Thus, even for relatively closely related viruses, the envelope glycoproteins, while serving the same function, have markedly different structural properties.

These markedly different primary, secondary, tertiary, and quaternary structures affect heterologous expression characteristics. In fact, in contrast to HIV envelope glycoprotein which is expressed at reasonable efficiency in both the Chinese Hamster Ovary (CHO) cell expression system (Berman et al. J Virol (1989) 63:3489–98) and the Drosophila cell expressoin system (Culp et al.), the dengue virus envelope glycoprotein is not efficiently in CHO but is efficiently expressed in the Drosophila system. Expression levels of dengue envelope in CHO being less than 0.1 mg/L.

Recombinant flavivirus E glycoprotein has been expressed in several systems to date (See Putnak, 1994 for recent review). In general the systems have proven unsatisfactory for production of a cost-effective flavivirus vaccine due to limitations in antigen quality, quantity, or both. The following paragraphs highlight the major flavivirus vaccine efforts and summarize the results obtained to date.

Most efforts using Escherichia coli have yielded poor immunogen incapable of eliciting neutralizing antibodies in mice. This may reflect non-native conformation of flavivirus proteins expressed by bacteria and the necessity to process the viral proteins through the secretion pathway in order to achieve proper do sulfide bond formation and glycosylation. Expression of dengue proteins using the eucaryotic yeasts *Saccharomyces cerevisiae* and *Pichia pastoris* results in less than desirable quantities of immunogenic recombinant product obtained. The expression levels of dengue E achieved in these systems are well below that which would be required to produce a cost-effective flavivirus vaccine. (John Ivy et al., unpublished data. Expression of 80% E in the above-mentioned yeast systems and fungal systems (*Neurospora crassa*) gave products that were highly glycosylated (contain extensive high mannose chains) which interferes with immunogenicity. Also, the yields were quite low (ranging from about 10–100 ng/ml (despite the ability of these systems to produce high yields generally).)

Attempts to express 80% E in the Chinese Hamster Ovary (CHO) cells expression system were particularly disappointing. Predictions that this mammalian expression normally infects mammals and the system supports all the necessary post-translational modifications required to get native confirmation, were wrong. In fact the yields were poorest of any system (less than 0.1 μg/ml) and the Dengue envelope gene was completely unstable in this expression system.

Use of the baculovirus expression system for flavivirus subunit vaccine production has met with limited success (Reviewed in Putnak, Modern Vaccinology, 1994). In contrast to the high expression levels reported for various heterologous proteins in the baculovirus system, the levels of expression of flavivirus structural proteins were quite low (e.g. 5–10 μg DEN-2 E/$10^6$ cells; Deubel et al., 1991), and reactivity against a panel of anti-flaviviral monoclonal antibodies (MAbs) indicated that many conformationally sensitive epitopes were not present (Deubel et al., 1991). This suggests that folding of recombinant E produced in the baculovirus system may differ from the natural viral E protein. Furthermore, immunization with baculovirus-expressed recombinant envelope protein from DEN-1 (Putnak et al., 1991), Japanese Encephalitis virus (McCown et al., 1990), or Yellow Fever virus (Despres et al., 1991) failed to elicit substantial titers of virus neutralizing antibodies or protection against viral challenge in mice.

Several reports have described vaccinia-flavivirus recombinants expressing envelope proteins as part of a polyprotein. The most consistently successful results in vaccinia expression of flaviviral proteins have been obtained co-expressing prM and E. Mice immunized with recombinant vaccinia expressing Japanese Encephalitis (JE) virus prM and E developed higher neutralizing antibody titers and survived higher challenge doses of virus (<10,000 $LD_{50}$; Konishi et al, 1992) than mice immunized with recombinant vaccinia virus expressing E alone (<10 $LD_{50}$; Mason et al, 1991). Similarly, mice immunized with a vaccinia-Yellow Fever (YF) virus recombinant expressing prM-E were protected from virus challenge at levels equivalent to that of the attenuated YFV-17D vaccine, while vaccinia-YF virus recombinants expressing E-NS1, C-prM-E-NS1, or NS1 failed to protect mice (Pincus et al, 1992). Vaccinia DEN-1 recombinants expressing prM-E elicited neutralizing and hemagglutination inhibiting antibodies in mice, while recombinants expressing DEN-1 C-prM-E-NS1-NS2a-NS2b elicited no E-specific immune response (Fonseca et al, 1994).

Coordinate synthesis of prM and E appears to be important to obtain the native conformation of E. Expression of E in the absence of prM may result in a recombinant product that presents a different set of epitopes than those of the native virion (Konishi and Mason 1993; Heinz et al, 1994; Matsuura et al, 1989). Epitope mapping of the E expressed with prM suggests that the co-expressed protein more closely resembles the native virus. As prM and E appear to form heterodimers during viral maturation and E undergoes an acid pH-induced conformational change, Heinz et al (1994) has suggested the association of prM and E is required to prevent irreversible pH-induced conformational changes during transit through the secretory pathway. However, it has been shown that carboxy-truncated forms of flavivirus E expressed in the absence of prM elicit protection from challenge (Men et al, 1991; Jan et al, 1993; Coller et al., in preparation), suggesting expression of E in the absence of prM can result in the display of protective epitopes.

Within the last ten years an alternative eucaryotic expression system which uses the *Drosophila melanogaster* Schneider 2 (S2) cell line has been developed and used to efficiently express the envelope glycoprotein of Human Immunodeficiency Virus (Ivey-Hoyle et al., 1991; Culp et al, 1991; van der Straten et al, 1989). We have applied this system to production of recombinant flavivirus subunit polypeptides and have found the system can easily produce 20–30 mg of recombinant protein per liter of medium (unpublished). The recombinant product we have focused most of our efforts on is a soluble form of flaviviral E, which is truncated at the carboxy-terminal end resulting in a polypeptide which represents approximately 80% of the full-length E molecule (amino acids 1–395; 80% E). We have expressed 80% E as a single open-reading frame with prM to enhance proper folding and secretion as described above. The expression levels achieved using this combination of expression system and recombinant DNA construct far exceed those achieved in other systems and does provide a cost-effective source of flaviviral antigen for vaccine production. In addition, we have demonstrated that the recombinant 80% E product secreted by these cells is capable of inducing neutralizing antibodies and protection in mice (Coller et al., in preparation.)

In two instances, however, applicants failed in their attempt to produce envelope glycoproteins in the Drosophila expression system. First, a 100-amino acid polypeptide which is a unique domain (Domain B; amino acids 296–395 of DEN-2E) within the 80% E molecule was expressed poorly in the Drosophila expression system. The expression levels for Domain B were significantly lower (less than 1 mg/l) than those achieved with 80% E (approximately 15 mg/l). Domain B was the most likely expressed polypeptide in *S. cereviseae* and *P. pastoris* which we evaluated with expression levels up to 575 mg/l for Domain B expressed in *P. pastoris* (compared to expression levels of approximately 1 mg/l for 80% E). Second, a truncated version of the measles hemagglutinin protein (90% HA) was expressed and secreted at very low levels in the Drosophila expression system (about 0.5 mg/l). Like dengue, measles has been refractory to stable expression in many systems (Hirano, A. et al. "Generation of mammalian cells expressing stably measles virus protein via bicistronic RNA," Journal of Virological Methods (1991) 33:135–147).

The two examples above show that protein expression is highly unpredictable (Goeddel, D. V. "Systems for Heterologous Gene Expression," in *Methods in Enzymology,* Vol. 185, pp. 3- Academic Press, Inc., 1990). In this case, protein expression is further complicated by the complexity of expressing bioenvelope glycoproteins (Mustilli, A. C. et al. "Comparison of secretion of a hepatitis C virus glycoprotein in *Saccharomyces cerevisiae* and *Kluyveromyces lactis,*" *Res Microbiol* (1999) 150:179–187).

Over the past approximately eight years of research relating to dengue 80% E, the assignee of the present application has spent over $6.5 million to arrive at the invention.

While the use of this combination of Drosophila S2 cells and prM80% E has allowed significant progress towards the production of an effective flavivirus vaccine, the ability of a small polypeptide, with limited antigenic complexity, to induce long term, protective immunity in a large, outbred population may be limited. Numerous studies have demonstrated that immunogenicity is directly related both to the size of the immunogen and to the antigenic complexity of the immunogen. Thus, in general, larger antigens make better immunogens. In addition, the structure of TBE envelope protein was recently solved (Rey et al., 1995) and this analysis revealed that the native form of E protein found on the surface of the virion is a homodimer (FIG. 1). Our recombinant flaviviral E protein discussed above is monomeric and therefore is not identical to the natural viral E protein. Thus, in an attempt to produce a recombinant flavivirus vaccine with enhanced immunogenicity we engineered several constructs designed to promote dimerization of the soluble 80% E which is so efficiently produced in the Drosophila cells. By enhancing dimerization we increase the potency of the vaccine by increasing the structural similarity to native, virally expressed E, as well as by increasing the size and antigenic complexity of the immunogen.

Several of the approaches we have adopted to enhance dimerization of soluble 80% E were originally developed for antibody engineering. Flexible peptide linkers have been used to link the variable heavy and variable light chain polypeptides in the engineering of single chain Fv's (scFv; Huston et al., 1988; Bird et al., 1988). These linkers, which are often repeated GlyGlyGlyGlySer (Gly4Ser) unit (SEQ ID NO:1), exhibit limited torsional constraints on the linked polypeptides, and therefore offer a reasonable option for covalently connecting the carboxy end of one 80% E moiety to the amino terminus of the second 80% E moiety. Based on the distance from the carboxy terminus of one subunit and the amino terminus of the other in the crystal structure of TBE 80% E dimers (F. Heinz, personal communication), we designed a peptide linker, made up predominantly of Gly4Ser repeats, to link the two 80% E molecules. The linker was designed to be slightly longer than the distance in the native molecule, in order to avoid torsional constraint on the association of the two 80% E moieties.

The second and third approaches to engineer 80% E dimers used strategies developed to engineer self-associating scFv miniantibodies. For homodimer miniantibody expression, Pack et al. (1992; 1993) expressed the scFv as a fusion with a flexible linker hinge and one of two dimerization domains (FIG. 2). One dimerization domain was a parallel coiled-coil helix of a leucine zipper from the yeast GCN4 gene product (Landschulz et al., 1988; O'Shea et al., 1989). The other domain was two alpha helices spaced by a sharp turn that associate to form a homodimeric four-helix bundle (Ho and DeGrado, 1987). The hinge region used to link the dimerization domains to the scFv was taken from an antibody hinge region to achieve maximum rotational flexibility. When these antibody-hinge-helix constructs were expressed in *E. coli*, homodimer miniantibodies spontaneously formed and could be extracted from the soluble protein fraction of cell lysates. These antibodies were indistinguishable from whole antibodies in functional affinity. To express secreted 80% E that can spontaneously dimerize, we have used these dimerization domains connected to the 80% E domains by a flexible Gly4Ser tether.

DISCLOSURE OF THE INVENTION

The present invention discloses and claims vaccines containing, as an active ingredient, a secreted recombinantly produced dimeric form of truncated flaviviral envelope protein. The vaccines are capable of eliciting the production of neutralizing antibodies against flavivirus. In the illustrations below, the dimeric forms of truncated flaviviral envelope protein are formed 1) by directly linking two tandem copies of 80% E in a head to tail fashion via a flexible tether; 2) via the formation of a leucine zipper domain through the homodimeric association of two leucine zipper helices each fused to the carboxy terminus of an 80% E molecule; or 3) via the formation of a non-covalently associated four-helix bundle domain formed upon association of two helix-turn-helix moieties each attached to the carboxy terminus of an 80% E molecule. All products are expressed as a polyprotein including prM and the modified 80% E products are secreted from Drosophila melanogaster Schneider 2 cells using the human tissue plasminogen activator secretion signal sequence (tPAL). Secreted products are generally more easily purified than those expressed intracellularly, facilitating vaccine production.

One embodiment of the present invention is directed to a vaccine for protection of a subject against infection by a Flavivirus. The vaccine contains, as active ingredient, the dimeric form of truncated envelope (E) protein of a flaviviral serotype, for example a dengue virus serotype. The dimeric truncated E is secreted as a recombinantly produced protein from eucaryotic cells. The vaccine may further contain portions of additional flaviviral serotype dimeric E proteins similarly produced. A preferred embodiment of the present invention relates to a vaccine for the protection of a subject against infection by a dengue virus. The vaccine contains a therapeutically effective amount of a dimeric 80% E, where, the 80% E has been secreted as a recombinantly produced protein from eucaryotic cells, such as Drosophila cells. Further, the "80% E" refers in one instance to a polypeptide which spans from Met 1 to Gly 395 of the DEN-2 envelope protein. The sequences described in the present application represent the envelope protein from dengue type 2 virus; three additional distinct dengue serotypes have been recognized. Therefore, "80% E" also refers to the corresponding peptide region of the envelope protein of these serotypes, and to any naturally occurring variants, as well as corresponding peptide regions of the envelope (E) protein of other flaviviruses. For example, serotypes of dengue virus such as: DEN-1; DEN-2; DEN-3; and DEN-4, as well as serotypes of: Japanese encephalitis virus (JE), Tick-borne encephalitis virus (TBE), West Nile virus (WN), and the family prototype, Yellow fever virus (YF).

Other embodiments of the present invention are directed to three basic approaches for the construction of dimeric 80% E molecules. (See infra.) These include: linked 80% E dimer; 80% E ZipperI; 80% E ZipperII; and 80% E Bundle.

Still other embodiments of the present invention are directed to vaccines containing truncated envelope protein of dimeric 80% E of more than one serotype to form multivalent vaccines, (i.e., divalent, trivalent, tetravalent, etc.). For example, such embodiments of the present invention include: a vaccine containing a first dimeric 80% E product of one flaviviral serotype and a second dimeric 80% E product of a second flaviviral serotype, and a third dimeric 80% E product of a third flaviviral serotype and a fourth dimeric 80% E product of a fourth flaviviral serotype, as well as in combination with other dimeric 80% E, each of a separate serotype one from another, where all dimeric 80% Es have been secreted as recombinantly produced protein from eucaryotic cells, such as Drosophila cells. It is considered that the present invention clearly includes vaccines that are comprised of multivalent truncated envelope protein of dimeric 80% E, which embrace two, three, four or more serotypes. For example, these serotypes may include the following dengue virus serotypes: DEN-1; DEN-2; DEN-3; and DEN-4, as well as other flavivirus serotypes of: Japanese encephalitis virus (JE), Tick-borne encephalitis virus (TBE), West Nile virus (WN), and the family prototype, Yellow fever virus (YF).

Additional embodiments of the present invention contemplate compositions of antibodies consisting essentially of antibodies generated in a mammalian subject administered an immunogenic amount of a vaccine containing dimeric 80% E as well as containing a first dimeric 80% E and a second dimeric 80% E, where both first and second dimeric 80% E have been secreted as recombinantly produced protein from eucaryotic cells, such as Drosophila cells. These vaccines could include multivalent truncated envelope protein of dimeric 80% E, which embrace two, three, four or more serotypes. These serotypes may include dengue virus serotypes: DEN-1; DEN-2; DEN-3; and DEN-4, as well as serotypes of: Japanese encephalitis virus (JE), Tick-borne encephalitis virus (TBE), West Nile virus (WN), and the family prototype, Yellow fever virus (YF).

Still other embodiments of the present invention are drawn to immortalized B cell lines, where the B cells have been generated in response to the administration to a mammalian subject of an immunogenic amount of a vaccine containing truncated envelope protein of dimeric 80% E of more than one serotype to form multivalent vaccines, (i.e., divalent, trivalent, tetravalent, etc.). For example, such embodiments of the present invention include: a vaccine containing a first dimeric 80% E product of one flaviviral serotype and a second dimeric 80% E product of a second flaviviral serotype, and a third dimeric 80% E product of a third flaviviral serotype and a fourth dimeric 80% E product of a fourth flaviviral serotype, as well as in combination with other dimeric 80% E, each of a separate serotype one from another, where all dimeric 80% Es have been secreted as recombinantly produced protein from eucaryotic cells, such as Drosophila cells. These vaccines could include multivalent truncated envelope protein of dimeric 80% E, which embrace two, three, four or more serotypes. These serotypes may include dengue virus serotypes: DEN-1; DEN-2; DEN-3; and DEN-4, as well as serotypes of: Japanese encephalitis virus (JE), Tick-borne encephalitis virus (TBE), West Nile virus (WN), and the family prototype, Yellow fever virus (YF).

Further embodiments of the present invention are drawn to monoclonal antibodies secreted by these immortalized B cell lines.

Still further embodiments of the present invention are drawn to methods to protect a subject against a Flavivirus. These methods include the step of administering in a suitable manner to a subject in need of such protection an effective amount of a vaccine containing dimeric 80% E on a schedule optimum for eliciting such a protective immunoreactive response.

Another embodiment of the present invention is directed to methods to utilize the dimeric form of truncated flavivirus envelope protein for diagnosis of infection in individuals at risk for the disease. The diagnostic contains, as active ingredient, the dimeric form of truncated envelope protein of a flavivirus serotype. The dimeric truncated E is secreted as a recombinantly produced protein from eucaryotic cells. The diagnostic may further contain portions of additional flavivirus serotype dimeric E proteins similarly produced.

A preferred embodiment of the present invention relates to an immunodiagnostic for the detection of a Flavivirus, where the immunodiagnostic contains, a dimeric 80% E that has been secreted as a recombinantly produced protein from eucaryotic cells, such as Drosophila cells. Specifically, a preferred embodiment of the present invention relates to an immunodiagnostic for the detection of a flavivirus. Embodiments of the present invention include immunodiagnostics for the detection of a Flavivirus, where the immunodiagnostic contains, dimeric 80% E of more than one serotype to form multivalent immunodiagnostics, (i.e., divalent, trivalent, tetravalent, etc.). For example, such embodiments of the present invention include: an immunodiagnostics containing a first dimeric 80% E product of one flaviviral serotype and a second dimeric 80% E product of a second flaviviral serotype, and a third dimeric 80% E product of a third flaviviral serotype and a fourth dimeric 80% E product of a fourth flaviviral serotype, as well as in combination with other dimeric 80% E, each of a separate serotype one from another, where all of the dimeric 80% Es have been secreted as recombinantly produced protein from eucaryotic cells, such as Drosophila cells.

The present invention includes the embodiments of immunodiagnostic kits for the detection of a Flavivirus, in a test subject. These immmunodiagnostic kits contain (a) dimeric 80% E, where the dimeric 80% E has been secreted as recombinantly produced protein from eucaryotic cells, such as Drosophila cells; (b) a suitable solid support phase coated with dimeric 80% E; and (c) labeled antibodies immunoreactive to antibodies from the test subject.

Other embodiments of the immunodiagnostic kits of the present invention include multivalent dimeric 80% E of more than one serotype to form multivalent immunodiagnostics, (i.e., divalent, trivalent, tetravalent, etc.). For example, such embodiments of the present invention include: an immunodiagnostics containing a first dimeric 80% E product of one flaviviral serotype and a second dimeric 80% E product of a second flaviviral serotype, and a third dimeric 80% E product of a third flaviviral serotype and a fourth dimeric 80% E product of a fourth flaviviral serotype, as well as in combination with other dimeric 80% E products, each of a separate serotype one from another, where all of the dimeric 80% E products have been secreted as recombinantly produced protein from eucaryotic cells, such as Drosophila cells.

Further embodiments of the present invention relate to compositions of matter, that include a vector host recombinant DNA expression system, containing: (a) a suitable eucaryotic host cell; (b) a suitable recombinant DNA expression vector; (c) DNA encoding dimeric 80% E, operably linked and under the control of a suitable promoter; and (d) where the DNA encoding dimeric 80% E is also operably linked to a secretory signal leader sequence. The present invention further includes embodiments of a vector host recombinant DNA system where the dimeric 80% E is selected from the group consisting of: linked 80% E dimer; 80% E ZipperI; 80% E ZipperII; and 80% E Bundle. A preferred embodiment of the present invention relates to a vector host recombinant DNA system where the eucaryotic host cell is a Drosophila cell.

Other compositions of matter embodied in the present invention include DNA sequences encoding dimeric 80% E, specifically including DNA sequences encoding: linked 80% E dimer; 80% E ZipperI; 80% E ZipperII; and 80% E Bundle.

BRIEF DESCRIPTION OF THE DRAWINGS

FIG. 1 is a drawing reproduced from Rey et al., showing the crystal structure of the envelope protein of Tick Borne Encephalitis virus.

FIG. 2 is a drawing reproduced from Pack et al., which shows two the approaches used for miniantibody engineering applied to 80% E Dimer formation.

FIGS. 3A–3D show the partial nucleotide sequence (SEQ ID NO:2) and deduced amino acid sequence (SEQ ID NO:3) of the genome of DEN-2 PR159/S1 strain.

FIG. 7 illustrates the cloning strategy used to introduce oligonucleotides encoding the leucine zipper and four-helix bundle dimerization domains into the linked 80% E dimer cDNA clone.

Figures 10A, 10B:
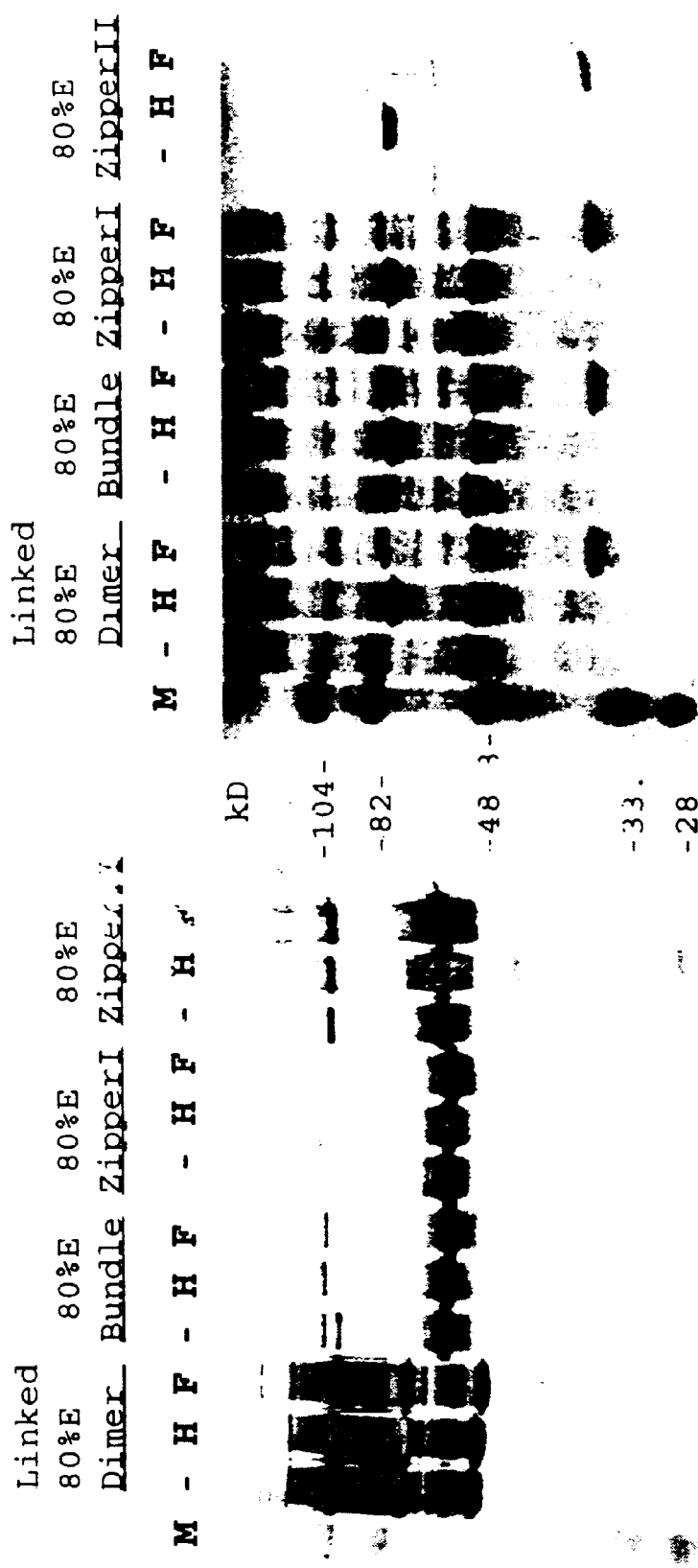

FIGS. 10A–10B demonstrate the glycosylation of the secreted dimeric 80% E products by SDS-PAGE analysis of endoglycosidase-digested 80% E dimers.

Figures 11A, 11B:
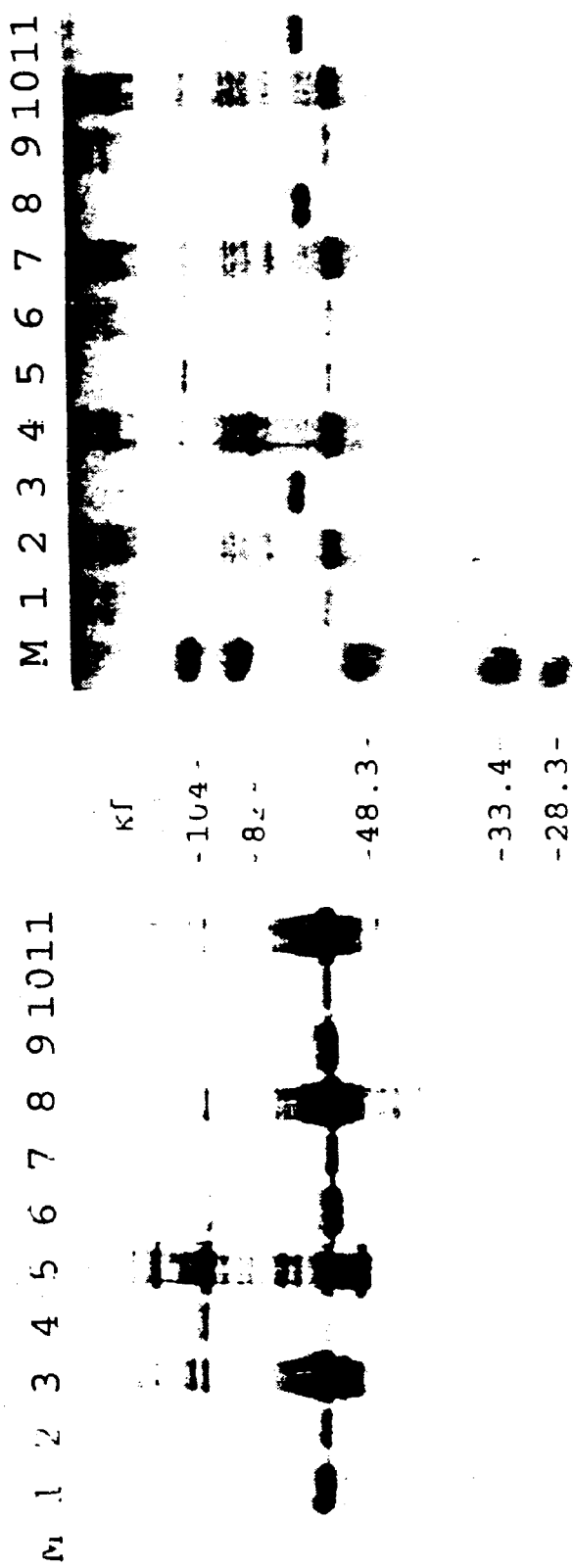

FIGS. 11A–11B demonstrate the application of immunoaffinity techniques to purification of the secreted dimeric 80% E products.

Figure 12:
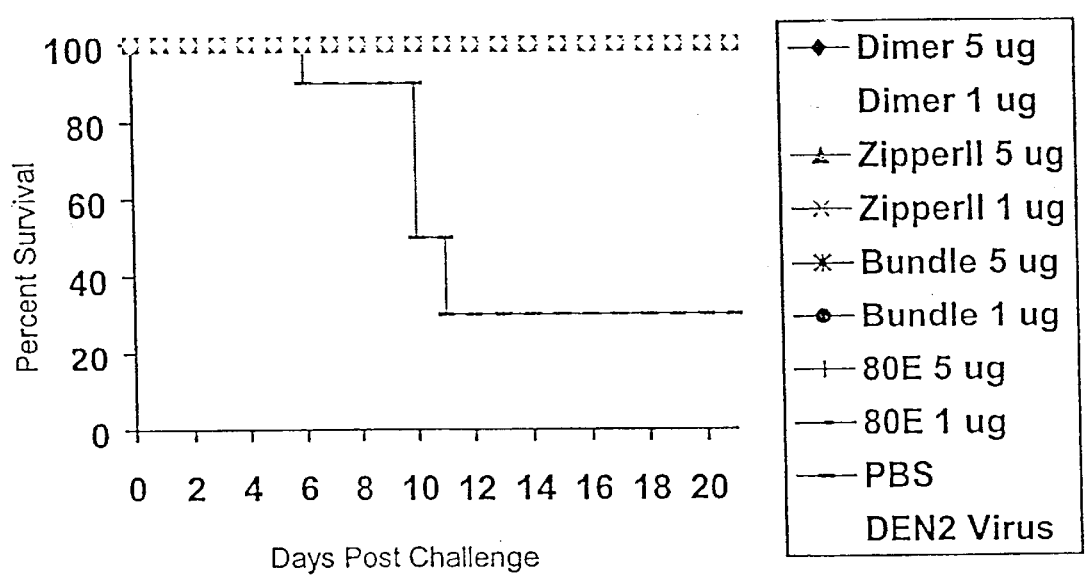

FIG. 12 Protection of Suckling Mice Immunized with Recombinant Dimeric and Monomeric DEN-2 80% Proteins from Viral Challenge.

MODES OF CARRYING OUT THE INVENTION

The invention provides, for the first time, a subunit vaccine with increased immunogenicity that can be efficiently produced and secreted using a recombinant expression system and that is effective in inducing a strong virus neutralizing response to flaviviruses. Although many attempts have been made to obtain such a subunit vaccine, previous studies were plagued with either low expression levels of an effective immunogen or efficient production of an ineffective vaccine candidate. The present applicants have found that recombinantly-engineered, dimeric forms of a carboxy-terminally truncated flaviviral envelope protein, corresponding to amino acids 1–395, are efficiently secreted by certain convenient eucaryotic recombinant hosts, in a form that permits processing to mimic the native conformation of the protein. The efficient secretion of the proteins into the culture medium facilitates purification. Furthermore, the secreted forms are able, especially when administered in the presence of adjuvant, to raise high titer virus neutralizing antibodies in animals. Thus, these proteins represents a useful component of a vaccine for protecting subjects against flaviviral infection. As used herein, "80% E" refers in one instance to a polypeptide which spans from Met 1 to Gly 395 of the DEN-2 envelope protein. The sequences described in the present application represent the envelope protein from dengue type 2 virus; three additional distinct dengue serotypes have been recognized. Therefore, "80% E" also refers to the corresponding peptide region of the envelope protein of these serotypes, and to any naturally occurring variants, as well as corresponding peptide regions of the envelope (E) protein of other flaviviruses. For example, serotypes of dengue virus such as: DEN-1; DEN-2; DEN-3; and DEN-4, as well as serotypes of: Japanese encephalitis virus (JE), Tick-borne encephalitis virus (TBE), West Nile virus (WN), and the family prototype, Yellow fever virus (YF). The modifications made to the 80% E products by addition of carboxy-terminal sequences encoding flexible linkers, leucine zipper domains, or four helix bundle domains, designed to enhance the dimerization of the 80% E molecules, are described in detail below. All of these dimeric 80% E proteins are produced from vectors containing the DNA encoding the flavivirus prM as a fusion with mature proteins resulting in secretion of the processed, mature dimeric 80% E proteins from which the prM protein has been removed.

Three basic approaches have been used to construct dimeric 80% E molecules. The first approach involves using tandem copies of 80% E covalently attached to each other by a flexible linker. As used herein, "Linked 80% E Dimer" refers in one instance to a polypeptide which encodes DEN-2 80% E—GGGSGGGGSGGGTGGGSGGGSGG GG—DEN-2 80% E (SEQ ID NO:4). The stretch of amino acids covalently linking the two copies of DEN2 80% E is designed to serve as a flexible tether allowing the two 80% E molecules to associate in native head-to-tail dimeric orientation while maintaining their covalent attachment to each other. The sequences described in the present application represent the envelope protein from dengue type 2 virus; three additional distinct dengue serotypes have been recognized. Therefore, "Linked 80% E Dimer" also refers to the corresponding peptide region of the envelope protein of these serotypes, and to any naturally occurring variants, as well as corresponding peptide regions of the envelope (E) protein of other flaviviruses. For example, serotypes of dengue virus such as: DEN-1; DEN-2; DEN-3; and DEN-4, as well as serotypes of: Japanese encephalitis virus (JE), Tick-borne encephalitis virus (TBE), West Nile virus (WN), and the family prototype, Yellow fever virus (YF).

It would be readily apparent to one of ordinary skill in the art to select other linker sequences as well. The present invention is not limited to the specific disclosed linkers, but, to any amino acid sequence that would enable the two 80% E molecules to associate in native head to tail dimeric orientation while maintaining their covalent attachment to each other.

The second approach involves addition of a carboxy-terminal leucine zipper domain to monomeric 80% E to enhance dimerization between two 80% E-leucine zipper molecules. Two versions of this approach have been adopted. One version includes a disulfide bond linking the leucine zipper domains resulting in a covalently linked dimer product, while the other is based on the non-covalent association of the leucine zipper domains. As used herein "80% E ZipperI" refers in one instance to a polypeptide which encodes DEN-2 80% E—GGGSGGGGSGGGTG-GGSGGGSPRMKQLEDKVEELLSKN YHLENE-VARLKKLVGER (SEQ ID NO:5). The first 22 amino acids extending after the carboxy terminus of 80% E serve as flexible tether between 80% E and the adjacent leucine zipper domain. The leucine zipper domain is designed to dimerize with the identical sequence from another 80% E Zipper molecule. The formation of a non-covalently linked leucine zipper will enhance the dimerization of the 80% E molecules, which may associate in native head to tail conformation by virtue of the flexible linker connecting the 80% E molecules with the leucine zipper domain. The sequences described in the present application represent the envelope protein from dengue type 2 virus; three additional distinct dengue serotypes have been recognized. Therefore, "80% E ZipperI" also refers to the corresponding peptide region of the envelope protein of these serotypes, and to any naturally occurring variants, as well as corresponding peptide regions of the envelope (E) protein of other flaviviruses. For example, serotypes of dengue virus such as: DEN-1; DEN-2; DEN-3; and DEN-4, as well as serotypes of: Japanese encephalitis virus (JE), Tick-borne encephalitis virus (TBE), West Nile virus (WN), and the family prototype, Yellow fever virus (YF).

It would be readily apparent to one of ordinary skill in the art to select other leucine zipper sequences as well. The present invention is not limited to the specific disclosed leucine zipper sequences, but to any amino acid sequences that would enable the dimerization between identical sequences from another 80% E Zipper molecule.

As used herein "80% E ZipperII" refers in one instance to a polypeptide which encodes DEN-2 80% E—GGGSGGGGSGGGTGGGSGGGSP-RMKQLEDKVEELLSKN YHLENEVARLKKLVGERG-GCGG (SEQ ID NO:6). The first 22 amino acids extending after the carboxy terminus of 80% E serve as flexible tether between 80% E and the adjacent leucine zipper domain. The leucine zipper domain is designed to dimerize with the identical sequence from another 80% E Zipper molecule. The leucine zipper domain of 80% E ZipperII ends in a GGCGG sequence (SEQ ID NO:7) which facilitates disulfide bond formation between the two leucine zipper helices. Thus, once the leucine zipper dimerizes, a disulfide bond forms between the two ends, resulting in a covalently linked dimer product. The formation of a covalently linked leucine zipper will enhance the dimerization of the 80% E molecules, which may associate in native head to tail conformation by virtue of the flexible linker connecting the 80% E molecules with the leucine zipper domain. The sequences described in the present application represent the envelope protein from dengue type 2 virus; three additional distinct dengue serotypes have been recognized. Therefore, "80% E ZipperII" also refers to the corresponding peptide region of the envelope protein of these serotypes, and to any naturally occurring variants, as well as corresponding peptide regions of the envelope (E) protein of other flaviviruses. For example, serotypes of dengue virus such as: DEN-1; DEN-2; DEN-3; and DEN-4, as well as serotypes of: Japanese encephalitis virus (JE), Tick-borne encephalitis virus (TBE), West Nile virus (WN), and the family prototype, Yellow fever virus (YF).

It would be readily apparent to one of ordinary skill in the art to select other leucine zipper sequences as well. The present invention is not limited to the specific disclosed leucine sequences, but to any amino acid sequences that would permit the dimerizeration with an identical sequence from another 80% E Zipper molecule. Further, the ordinary skilled artisan would readily be able to determine other sequences that would facilitate do sulfide bond formation between the two leucine zipper helices.

The final approach used to enhance dimerization of 80% E is the addition of a helix-turn-helix domain to the carboxy terminal end of 80% E. The helix-turn-helix domain from one modified 80% E molecule will associate with that of another to form a dimeric four-helix bundle domain. As used herein "80% E Bundle" refers in one instance to a polypeptide which encodes DEN-2 80% E-GGGSGGGGSGGGTGGGSGGGSP-GELEELLKHLKELLKG-PRK-GELEELLKHLKELLKGEF (SEQ ID NO:8). The first 22 amino acids extending after the carboxy terminus of 80% E serve as flexible tether between the 80% E domain and the helix-turn-helix domain which follows. The formation of a non-covalently associated four helix bundle domain will enhance the dimerization of the 80% E molecules which may associate in the native head to tail conformation by virtue of the flexible linkers connecting 80% E to the helix bundle. The sequences described in the present application represent the envelope protein from dengue type 2 virus; three additional distinct dengue serotypes have been recognized. Therefore, "80% E Bundle" also refers to the corresponding peptide region of the envelope protein of these serotypes, and to any naturally occurring variants, as well as corresponding peptide regions of the envelope (E) protein of other flaviviruses. For example, serotypes of dengue virus such as: DEN-1; DEN-2; DEN-3; and DEN-4, as well as serotypes of: Japanese encephalitis virus (JE), Tick-borne encephalitis virus (TBE), West Nile virus (WN), and the family prototype, Yellow fever virus (YF).

It would be readily apparent to one of ordinary skill of the art to select other amino acid sequences that would form the flexible tether extending after the carboxy terminal of the 80% E and also comprising a helix-turn-helix domain. The present invention is not limited to the specific disclosed helix-turn-helix domains, but to any amino acid sequences that would enable the dimerization of one modified 80% E molecule through a non-covalent association with a second modified 80% E molecule. Further, the ordinary skilled artisan would readily be able to determine other sequences that would facilitate such non-covalent association of helices.

Recombinant techniques provide the most practical approach for practical large-scale production of these subunits for vaccine and diagnostic purposes. However, to be efficacious these proteins must undergo correct processing and assume a conformation similar to that of native flaviviral envelope protein. In order to achieve this, the recombinant production must be conducted in eucaryotic cells, preferably Drosophila melanogaster cells. Other eucaryotic cells including yeast, mammalian cells such as Chinese hamster ovary cells, or additional types of insect cells may also be used. However, to make a cost-effective vaccine feasible, the dimeric 80% E products must be efficiently secreted with correct processing and folding.

It has been found, as demonstrated herein below, that particularly efficient secretion of biologically active mature protein is most easily achieved using the Drosophila melanogaster Schneider-2 cell line. The expression of the dimeric products is driven by an efficient insect cell promoter (Drosophila metallothionein promoter) and secretion is targeted using a eucaryotic secretion leader (human tissue plasminogen activator secretion leader) as well as the flaviviral prM protein which contains the secretion signal for E. Other promoters and secretion leaders can also be used. In general, the invention includes expression systems that are operable in eucaryotic cells and which result in the secretion of dimeric truncated flaviviral envelope proteins into the medium. Thus, useful in the invention are cells and cell cultures which contain expression systems resulting in the production and secretion of mature dimeric truncated flaviviral envelope proteins.

The properly processed dimeric truncated E proteins are recovered from the cell culture medium, purified, and formulated into vaccines. Purification and vaccine formulation employ standard techniques and are matters of routine optimization. Suitable formulations are found, for example, in *Remington's Pharmaceutical Sciences*, latest edition, Mack Publishing Company, Easton, Pa. In particular, formulations will include an adjuvant, such as alum or other effective adjuvant. Alternatively, the active ingredient and the adjuvant may be coadministered in separate formulations.

The active vaccines of the invention can be used alone or in combination with other active vaccines such as those containing attenuated or killed forms of the virus, or those containing other active subunits to the extent that they become available. The vaccines may contain only one subunit as an active ingredient, or additional isolated active components may be added. Corresponding or different subunits from one or several serotypes may be included in a particular formulation.

To immunize subjects against flaviviral infection, the vaccines containing therapeutically effective amounts of the subunit are administered to the subject in conventional immunization protocols involving, usually, multiple administrations of the vaccine. Administration is typically by injection, typically intramuscular or subcutaneous injection; however, other systemic modes of administration may also be employed. Less frequently used, transmucosal and transdermal formulations are included within the scope of the invention as are effective means of oral administration. The efficacy of these formulations is a function of the development of formulation technology rather than the contribution of the present invention.

In addition to use in vaccines, the recombinant dimeric truncated E proteins of the invention may be used as analytical reagents in assessing the presence or absence of anti-flaviviral antibodies in samples. Such uses include, but are not limited to, diagnosis of infection with any flavivirus, such as dengue, monitoring the response to flaviviral infection, or use of immunoassays as part of standard laboratory procedures in the study of the progress of antibody formation or in epitope mapping and the like. The antigens are employed in standard immunoassay formats with standard detection systems such as enzyme-based, fluorescence-based, or isotope-based detection systems. Preferably, the antigen is used coupled to solid support or in sandwich assays, but a multiplicity of protocols is possible and standard in the art.

Thus, the secreted dimeric proteins, linked 80% E dimer, 80% E ZipperI, 80% E ZipperII, or 80% E Bundle, may be adsorbed onto solid support and the support then treated with a sample to be tested for the presence of anti-flaviviral antibodies. Unbound sample is removed, and any bound antibodies are detected using standard detection systems, for example, by treating the support with an anti-species antibody coupled to a detection reagent, for example horseradish peroxidase (HRP), with the species specificity of the antibody determined by the sample being tested. The presence of the HRP-conjugated antispecies antibody is then detected by supplying a suitable chromogenic substrate. In addition, the dimeric proteins may be used to detect the presence or absence of antibodies of various isotypes, including IgG and IgM isotypes by simply altering the specificity of the detecting antibodies. This may be particularly significant as IgM antibodies to flavivirus are considered diagnostic of a primary flaviviral infection. Alternatively, the anti-subunit or anti-flaviviral antibody may be adsorbed to the solid support and detected by treating the solid support with the recombinant dimeric proteins, either directly labeled, or labeled with an additional antibody in a sandwich-type assay.

In another embodiment, this invention relates to diagnostic kits comprising an antigen affixed to a solid support phase and an immunological detection system. The antigen of this invention is a secreted dimeric product used in conjunction with an immunological detection system. The antigen includes the recombinant dimeric truncated E protein in the form of a linked 80% E dimer or an 80% E ZipperI or an 80% E ZipperII or an 80% E bundle. The solid support phase of this invention relates to any of those found in the art, including microtiter plates. The detection system of this invention relates to any of those found in the art including antihuman antibodies conjugated with a detectable enzyme label.

In the examples below, the expression, secretion, processing, and immunogenicity of the secreted dimeric proteins, linked 80% E dimer, 80% E ZipperI, 80% E ZipperII, and 80% E Bundle are demonstrated. The products are recombinantly produced as modified prM-80% E fusions which are efficiently processed to remove the prM portion and secreted from Drosophila cells. The secreted dimeric 80% E products are secreted at high levels, up to 10 μlg/ml in unselected cells, and they display a complex pattern of glycosylation typical of mammalian and insect cell expression systems. Furthermore, based upon reactivity with conformationally sensitive monoclonal antibodies, the secreted dimeric 80% E products have native-like conformation and immunization of mice with dimeric 80% E, either crude or purified, induces a potent virus-neutralizing immune response.

The following examples are intended to illustrate but not to limit the invention.

EXAMPLE 1

Construction of Expression Vector pMttD2prM2X80E for Secretion of Linked 80% E Dimer DEN-2 strain PR159/S1 served as the source for all DEN-2 genes used in the invention. This strain has a small plaque, temperature-sensitive phenotype and differs from wild-type DEN-2 PR159 strain at only one amino acid in the prM and E coding regions. A cDNA clone, pC8 (Hahn et al, 1988), derived from DEN-2 strain PR159/S1 was used as starting material for generation of the subclones described below. The sequence of the clone has been previously published (Hahn et al., 1988), however, complete sequencing of the pC8 clone, as well as subclones derived from pC8, in our laboratory has identified a number of discrepancies with the published sequence. The complete nucleotide sequence and deduced amino acid sequence of the cDNA encoding the viral capsid, prM, E, and NS1 genes for PR159/S1 is included in FIG. 3. Shown in bold (and indicated with a *) at nucleotides 103, 1940, 1991, and 2025 are corrections to the Hahn published sequence.

The pC8 cDNA clone was used to generate several subclones critical for the construction of the dimeric 80% E clones included in this invention. The first subclone encodes amino acids 1–395 of E (80% E). The primers D2E937p and D2E2121m, shown below, were used to amplify the cDNA fragment extending from nucleotide 937 to 2121 and corresponding to 80% E. These primers include convenient restriction sites for cloning and the D2E2121m primer includes two stop codons after the 395th codon of E. The sequence of the primers is listed below with dengue sequence listed in uppercase letters and non-dengue sequences listed in lowercase letters.

```
                                     Bgl II
D2E937p (SEQ ID NO:9 and 10)    5'-cttctagatctcgagtacccgggacc ATG CGC TGC ATA GGA ATA TC -3'
                                   XbaI   XhoI    SmaI    Met Arg Cys Ile Gly Ile Ser Sal I
D2E2121m (SEQ ID NO:11 and 12)  5'-gctctagagtcga cta tta TCC TTT CTT GAA CCA G -3'
                                   XbaI          end end Gly Lys Lys Phe Trp
```

The amplified 80% E cDNA fragment was digested with XbaI and cloned into the NheI site of pBR322 to obtain the plasmid p29D280E. The complete nucleotide sequence of the clone was determined and a single, silent, PCR-induced mutation at nucleotide 2001 (AAC/Asn to AAT/Asn) was identified.

The portion of the genome that encodes prM and E was subcloned from pC8 using the Polymerase Chain Reaction (PCR). Oligonucleotide primers were designed to amplify the region of the genome, nucleotides 439 to 2421, corresponding to amino acids 1–166 of prM and 1–495 of F with convenient restriction sites engineered into the primers to facilitate cloning. In addition the primer used to amplify the amino terminus of the prM-E polyprotein includes a methionine codon (ATG) immediately preceding the first codon (phenylalanine) of the prM coding sequence. The sequence of the primers is listed below with dengue sequence listed in uppercase letters and non-dengue sequences listed in lowercase letters.

replaced with the 431 bp BamHI-SalI fragment from p29D280E, encoding the carboxy-terminal end of 80% E. The BamHI site is a naturally occurring site within the envelope cDNA, and the SalI site is an engineered site that immediately follows the stop codons encoded by the PCR primers. The resulting truncated cDNA clone, pBsD2prM80E, was confirmed by restriction digestion and DNA sequence analysis to encode amino acids 1 through 166 of prM and 1 through 395 of envelope.

To engineer the Linked 80% E Dimer, cDNA encoding 80% E was PCR amplified in two "halves" from pC8 using primer/adapters that include the flexible linker and a KpnI restriction endonuclease site to facilitate ligation of the two halves. One half designated PCR 1, encoded the carboxy terminus of the flexible linker and the amino terminus of 80% E. The other half designated PCR 2 encoded the carboxy terminus of 80% E and the amino terminus of the flexible linker. The nucleotide sequences of the primers used to amplify the PCR 1 and PCR 2 cDNAs are listed below.

```
                                              Bgl II
D2prM439p (SEQ ID NO:13 and 14)    5'-attctagatctcgagtacccgggacc atg TTT CAT CTG ACC ACA CGC -3'
                                          XbaI   XhoI    SmaI     Met Phe His Leu Thr Thr Arg Sal I
D2E2421m (SEQ ID NO:15 and 16)     5'-tctctagagtcga cta tta GGC CTG CAC CAT AAC TCC -3'
                                          XbaI       end end Ala Gln Val Met Val Gly
```

The PCR-generated prM100% E cDNA fragment was digested with the restriction endonuclease XbaI and ligated into the XbaI site of pBluescript SK+ (Stratagene, La Jolla, Calif.) to obtain the plasmid p29prME13. DNA sequence analysis of the PCR-generated cDNA clone identified two PCR-induced nucleotide differences between pC8 and p29prME13 in the prM-80% E coding region. The first mutation involves a T to C transition at nucleotide 1255 which is silent, and the second change involves an A to G transition at nucleotide 1117 which results in the conservative amino acid substitution of a valine for an isoleucine at position 61 of E. This mutation was repaired by replacing an AflII fragment containing the mutation with the corresponding AflII fragment from pC8 encoding the correct sequence.

In each case, the cDNA fragments spanned a naturally occurring, unique BamHI site within the 80% E coding region. The strategy for generating and cloning the fragments is outlined in FIG. 4. The PCR products were digested with PstI and BamHI and cloned individually into pUC plasmid vectors cut with the same two enzymes, resulting in plasmids pUC18PCR1 and pUC13PCR2 which were confirmed by DNA sequence analysis. The fragment encoding the amino terminus of 80% E was released from the pUC18PCR1 subclone by digestion with KpnI and cloned into pUC13PCR2 linearized with KpnI to generate the clone pUC13PCR2+1 which encodes the carboxy terminus of 80% E—flexible linker—amino terminus of 80% E.

The primers used to generate cDNA fragment PCR1 were: D180E-2N (SEQ ID NO:17 and 18)

```
                                       PstI  KpnI
DI80E-2N (SEQ ID NO:17 and 18)  5'AGTCCTGCAGGTACCGGTGGTGGTGGTTCTGGTGGTGGTTCTGGTGGTGGTATGCGTT
a.a. sequence                             T  G  G  G  G  S  G  G  G  S  G  G  G  M  R

GCATAGGAATATCAAATAGG
                                C  I  G  I  S  N  R

D2E2007M (SEQ ID NO:19 and 20)  5'CTATGATGATGTAGCTGTCTCC
a.a. sequence                      I  I  I  Y  S  D  G
```

To generate a cDNA subclone representing prM80% E, a 794 bp BamHI-SalI fragment, representing the carboxy-terminal end of E, was removed from p29prME13 and The primers used to generate cDNA product PCR 2 were: D180E-1C (SEQ ID NO:21 and 22)

```
                              PstI   KpnI
DI80E-1C (SEQ ID NO:21 and 22)  5'GCTCAGCTGCAGGTACCACCACCAGAACCACCACCACCAGAACCACCACCACC
a.a. sequence                              G  G  G  S  G  G  G  G  S  G  G  G  G

TTTCTTGAACCAGTCCAGC
                                 K  K  F  W  D  L

D2E1642P (SEQ ID NO:23 and 24)  GACACTGGTCACCTT
a.a. sequence                     T  L  V  T  F
```

Figure 1:
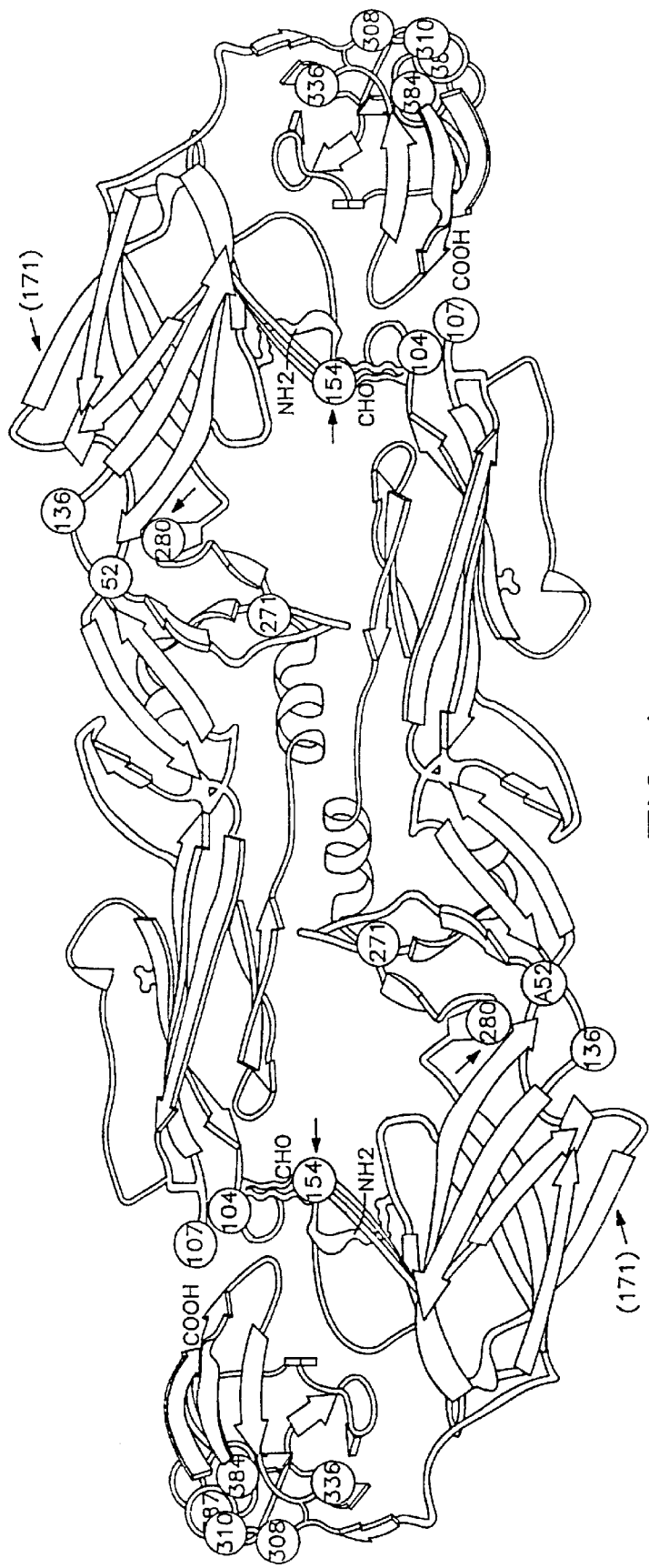
Figure 4:
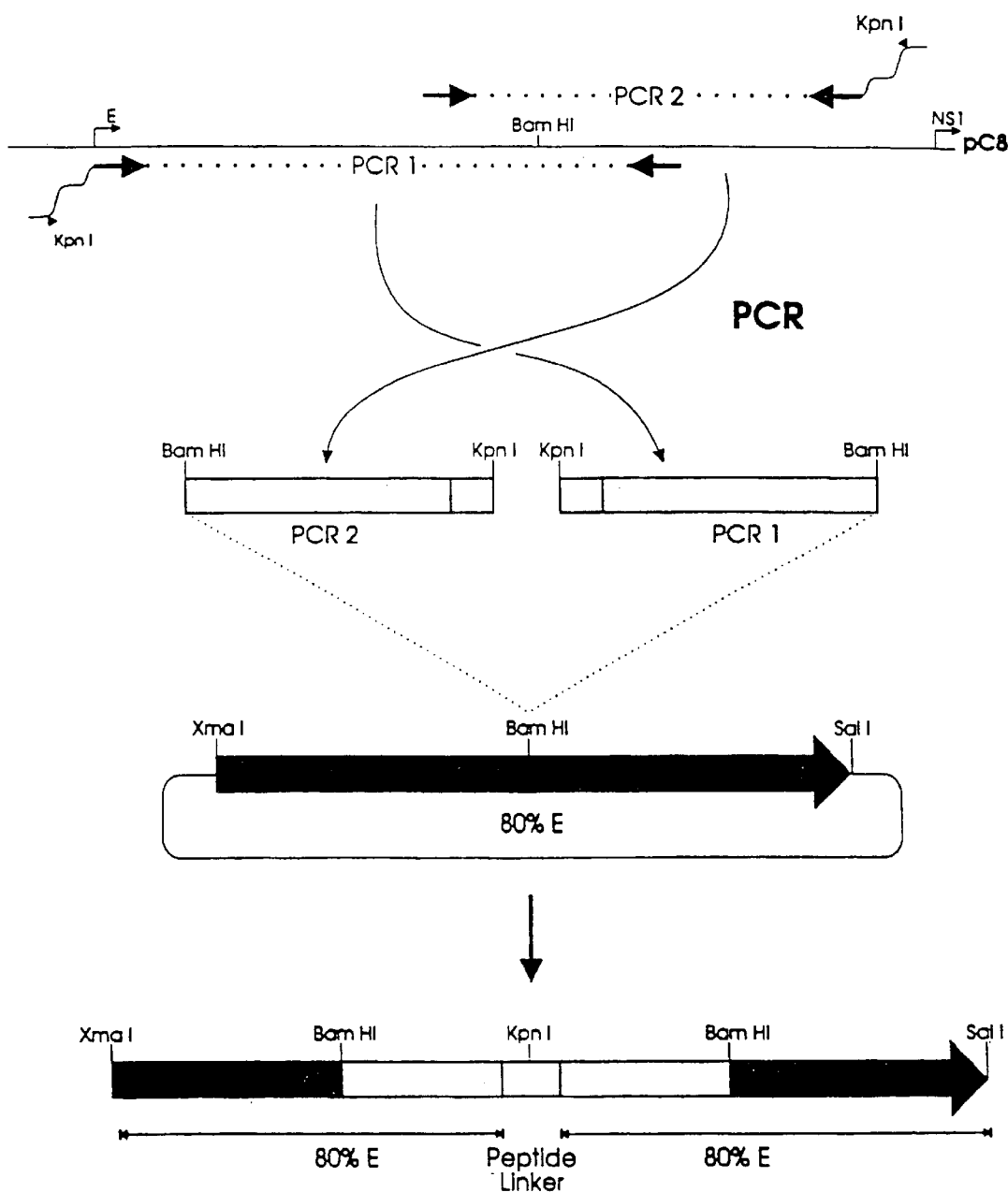
FIG. 4 is a drawing illustrating the strategy used to generate cDNA encoding tandem copies of 80% E linked by a flexible tether.
Figure 5:
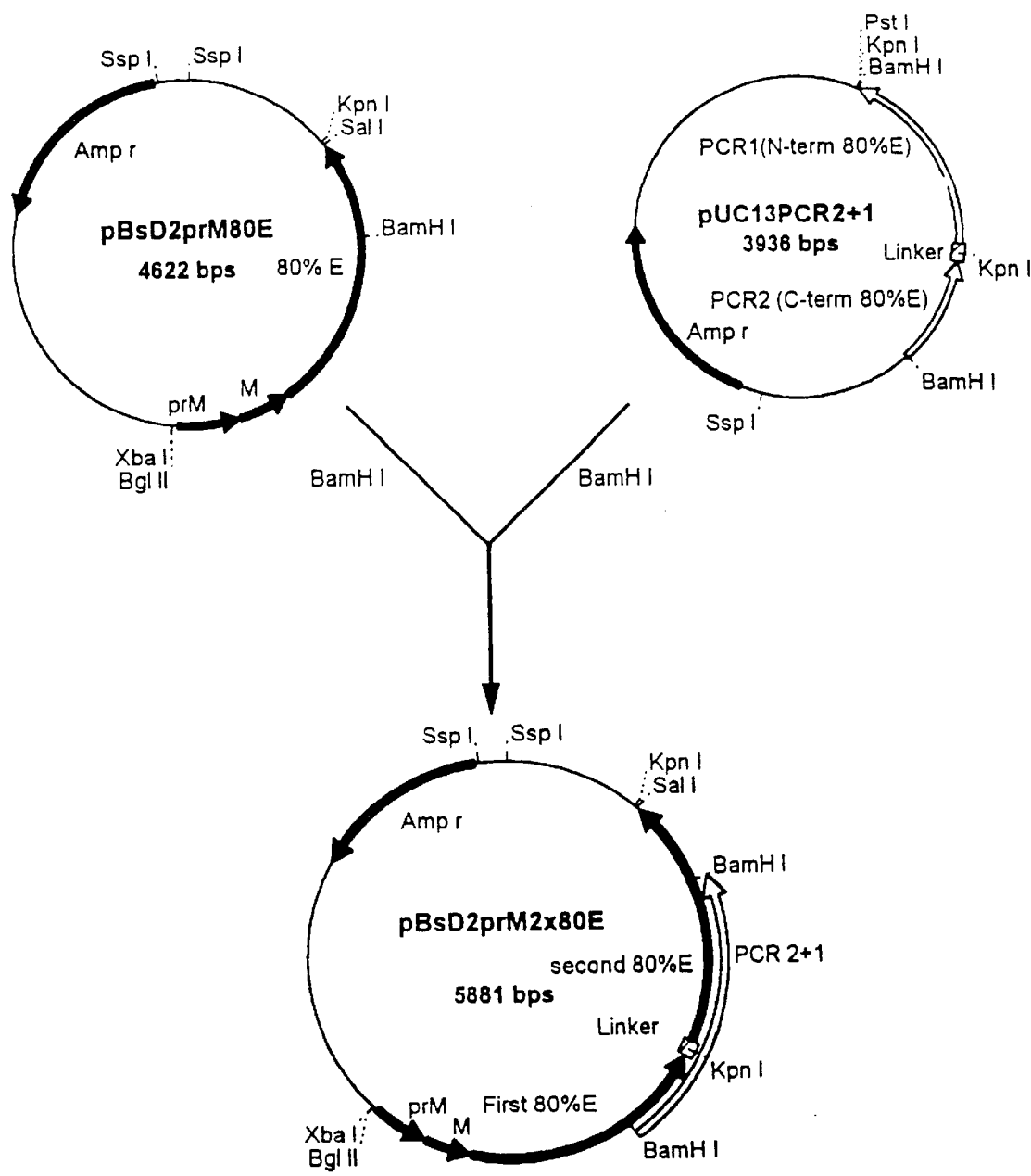
FIG. 5 is a drawing illustrating the cloning strategy used to introduce the carboxy-terminal portion of the first 80% E—linker—and amino terminal portion of the second 80% E molecule into a prM80% E cDNA clone.

To generate the sequence encoding prM plus the tandemly linked copies of 80% E, the cDNA fragment encoding carboxy terminus 80% E—flexible linker—amino terminus 80% E was released from the pUC13PCR2+1 clone by digestion with BamHI. This BamHI fragment was then ligated into pBsD2prM80E digested with BamHI to yield pBsD2prM2X80E (FIG. 5).

Figure 6:
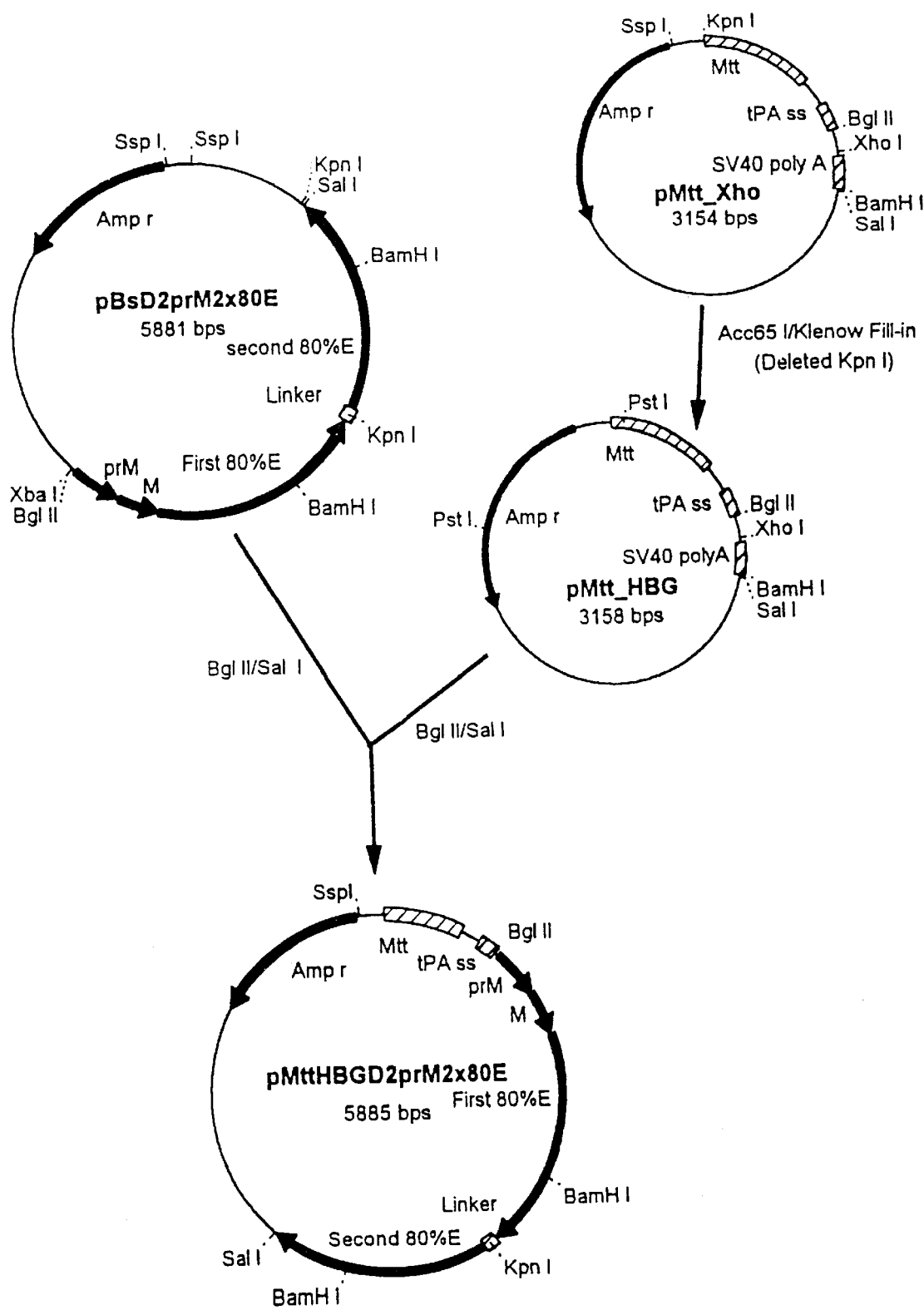
FIG. 6 is a drawing illustrating the cloning strategy used to introduce the linked tandem copies of 80% E into a Drosophila expression vector.

To facilitate manipulations of the linked 80% E dimer expression plasmid, we modified the *Drosophila melanogaster* expression vector pMttbns (SmithKline Beecham). A XhoI site at nucleotide 885 was deleted by removing a 19 base pair BamHI fragment containing the XhoI site. The resulting pMtt-Xho plasmid contained a unique XhoI site at nucleotide 730 which precedes the SV40 polyadenylation signal and is useful for introducing genes for expression studies. Plasmid pMtt-Xho was further modified to delete a KpnI site just upstream of the metallothionein promoter so that upon introduction of the linked 80% E dimer sequences, the KpnI site in the linker will be unique in the clone. To accomplish this, the pMtt-Xho plasmid was digested with the restriction endonuclease Acc65I. This enzyme has the same recognition sequence as KpnI but upon digestion results in a 5' overhang which can be made flush upon incubation with Klenow fragment of DNA polymerase I and deoxyribonucleotides. Thus digestion of pMtt-Xho with Acc65I followed with Klenow treatment and ligation resulted in a plasmid, pMtt-HBG, which lacks the KpnI site (FIG. 6).

Figure 8:
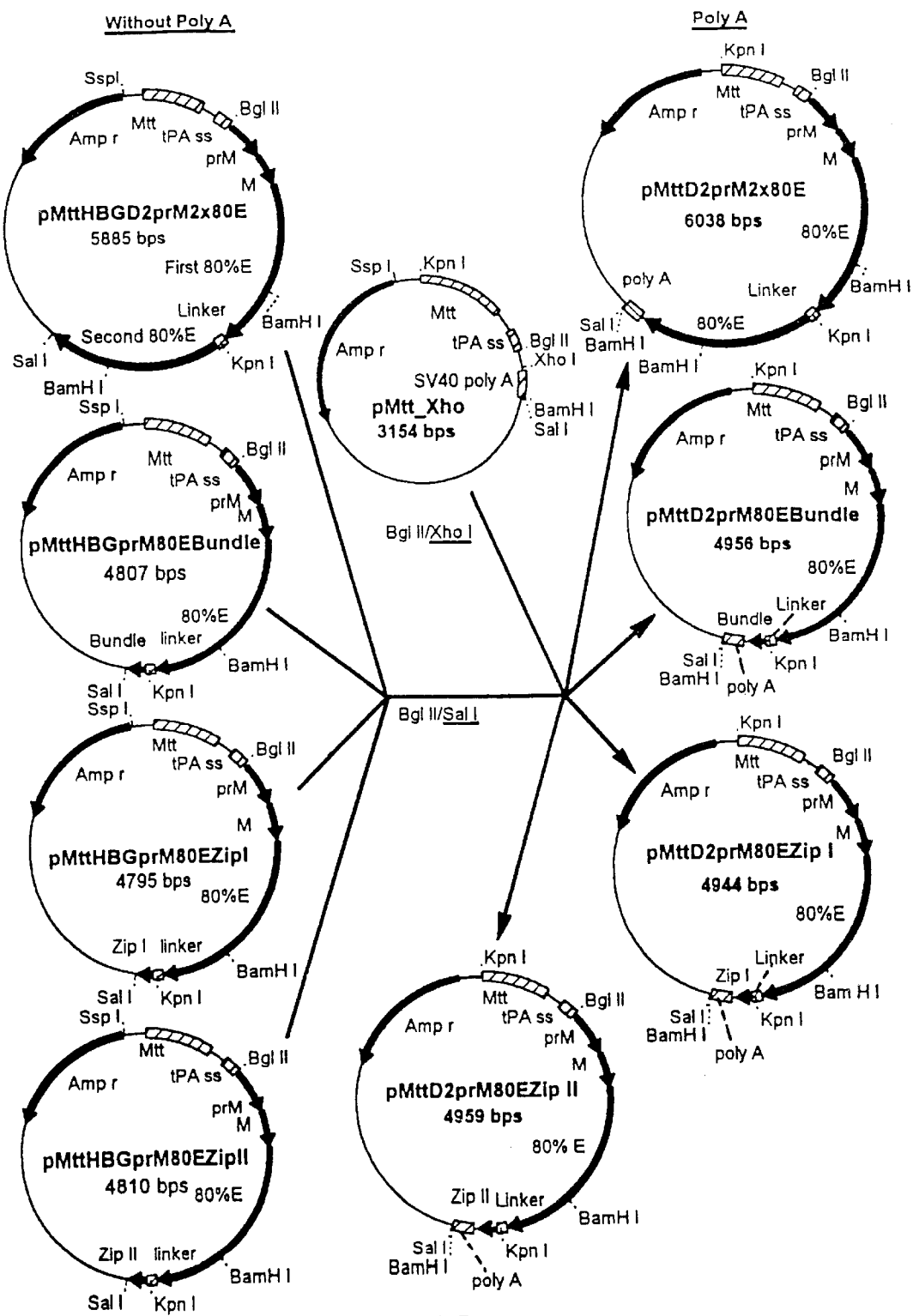
FIG. 8 is a drawing illustrating the cloning strategy used to introduce the cDNA fragments encoding Linked 80% E Dimer, 80% E ZipperI, 80% E ZipperII, and 80% E Bundle into a Drosophila expression vector.

To introduce the linked 80% E dimer into the pMtt-HBG expression plasmid, pBsD2prM2X80E was digested with BglII and SalI to release the prM—80% E—linker—80% E encoding fragment. This fragment was ligated into pMtt-HBG digested with BglII/SalI (FIG. 6). DNA sequence analysis of the resulting plasmid, pMttHBGD2prM2X80E, confirmed that the clone contained the entire prM2X80E coding sequence but lacked the SV40 polyadenylation signal. This clone is useful for introducing the oligonucleotides encoding the leucine zipper and four-helix bundle domains (Examples 2, 3, and 4) but is not useful for expression studies, as no poly A tail is associated with low expression levels. To restore the poly adenylation signal, the BglII/SalI fragment containing prM2X80E was removed from the pMttHBGD2prM2X80E clone and ligated into the pMtt-Xho plasmid digested with BglII and XhoI (FIG. 8). The resulting plasmid, pMttD2prM2X80E, was used for transfection of Drosophila cells and expression studies.

EXAMPLE 2

Figure 7:
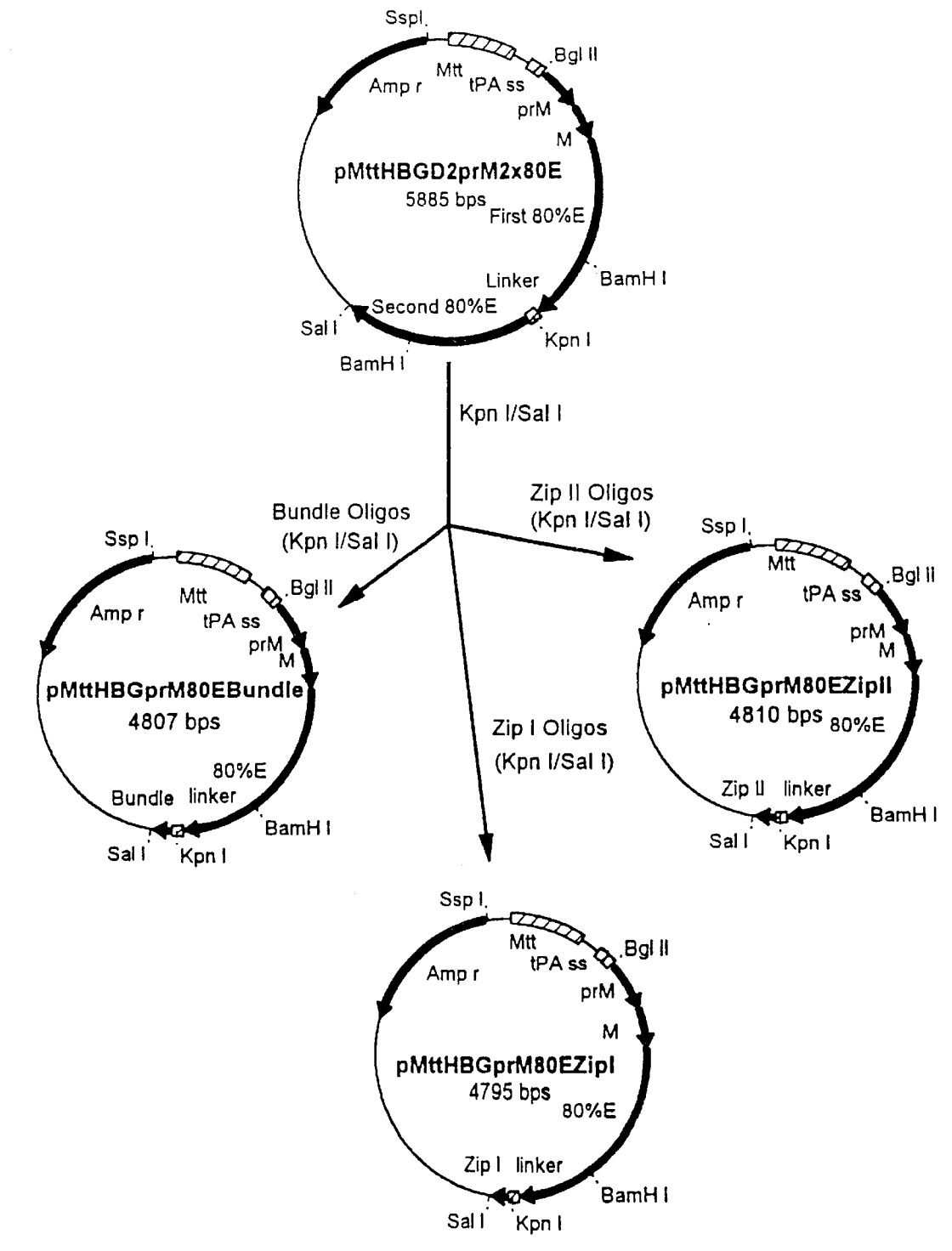

Construction of Expression Vector pMttD2prM80EZipperI for Secretion of Non-Covalently Linked 80% E ZipperI The plasmid pMttHBGD2prM2X80E was used as backbone for the introduction of oligonucleotides encoding one half of the flexible Gly4Ser linker and the leucine zipper coiled coil helix. As illustrated in FIG. 7, this plasmid was digested with KpnI and SalI to remove a fragment containing the carboxy-terminal half the flexible linker and the second copy of 80% E. Four overlapping oligonucleotides, coding for the carboxy-terminal half of the linker and leucine zipper helix were annealed to each other, generating a KpnI site at the 5' end and SalI site at the 3' end. The nucleotide and encoded amino acid sequence of the overlapping oligonucleotides are listed below. The annealed oligos were ligated into the KpnI/SalI digested vector to generate the expression plasmid, pMttHBGprM80EZipI. The identity of the pMttHBGprM80EZipI clone was confirmed by restriction digestion and limited sequence analysis.

As described above however, the pMttHBGD2prM2X80E used as backbone for this construct lacks the SV40 polyadenylation sequence. Therefore, the BglII/SalI fragment from pMttHBGprM80EZipI, encoding prM80% E ZipperI, was removed from the pMttHBGprM80EZipI plasmid and cloned into the BglII/XhoI digested pMtt-Xho vector to restore the downstream polyadenylation signal (FIG. 8). The resulting plasmid, pMttD2prM80EZipI, was confirmed by restriction digestion and sequence analysis and used to transfect Drosophila cells for expression studies.

Oligonucleotide Sequences: (DNA:SEQ ID NO:25, AA:SEQ ID NO:26, DNA-complementary strand: SEQ ID NO:27)

```
5' GTACCGGCGGTGGCTCCGGCGGTGGCTCCCCCCGCATGAAGCAGCTGGAGGACAAGGTGGA
3'     GCCGCCACCGAGGCCGCCACCGAGGGGGGCGTACTTCGTCGACCTCCTGTTCCACCTC
a.a.  T  G  G  S  G  G  G  S  P  R  M  K  Q  L  E  D  K  V  E

GAGCTGCTGTCCAAGAACTACCACCTGGAGAACGAGGTGGCCCGCCTGAAGAAGCTGGTGGGCGAGC
CTCGACGACAGGTTCTTCATGGTGGACCTCTTGCTCCACCGGGCGGACTTCTTCGACCACCCGCTCG
 E  L  L  S  K  N  Y  H  L  E  N  E  V  A  R  L  K  K  L  V  G  E

GCTAATAGG 3'
CGATTATCCAGCT 5'
 R
```

EXAMPLE 3

Construction of Expression Vector pMttD2prM80EZipperII for Secretion of Covalently Linked 80% E ZipperII The plasmid pMttHBGD2prM2X80E was used as backbone for the introduction of oligonucleotides encoding one half of the flexible Gly4Ser linker and the leucine zipper coiled coil helix with a cysteine residue close to the carboxy terminus. As illustrated in FIG. 7, this plasmid was digested with KpnI and SalI to remove a fragment containing carboxy-terminal half of the linker and the second copy of 80% E. Four overlapping oligonucleotides, coding for the carboxy-terminal half of the linker and cysteine-containing leucine zipper helix were annealed to each other, generating a KpnI site at the 5' end and SalI site at the 3' end. The nucleotide and encoded amino acid sequences of the overlapping oligonucleotides are listed below. The annealed oligos were ligated into the KpnI/SalI digested vector to generate the expression plasmid, pMttHBGprM80EZipII. The identity of the pMttHBGprM80EZipII clone was confirmed by restriction digestion and limited sequence analysis.

As described above however, the pMttHBGD2prM2X80E used as backbone for this construct lacks the SV40 polyadenylation sequence. Therefore, the BglII/SalI fragment from pMttHBGprM80EZipII, encoding prM80% E ZipperII, was removed from the pMttHBGprM80EZipII plasmid and cloned into the BglII/XhoI digested pMtt-Xho vector to restore the downstream polyadenylation signal (FIG. 8). The resulting plasmid, pMttD2prM80EZipII, was confirmed by restriction digestion and sequence analysis and used to transfect Drosophila cells for expression studies.

Oligonucleotide Sequences:(DNA:SEQ ID NO:28, AA:SEQ ID NO:29, DNA-complementary strand:SEQ ID NO:30)

EXAMPLE 4

Construction of Expression Vector pMttD2prM80EBundle for Secretion of Non-covalently Linked 80%E Bundle The plasmid pMttHBGD2prM2X80E was used as backbone for the introduction of oligonucleotides encoding one half of the flexible Gly4Ser linker and the helix-turn-helix domain. As illustrated in FIG. 7, this plasmid was digested with KpnI and SalI to remove a fragment containing the carboxy-terminal half of the linker and the second copy of 80%E. Four overlapping oligonucleotides, coding for the carboxy-terminal half of the linker and helix-turn-helix domain were annealed to each other, generating a KpnI site at the 5' end and SalI site at the 3' end. The nucleotide and encoded amino acid sequences of the overlapping oligonucleotides are listed below. The annealed oligos were ligated into the KpnI/SalI digested vector to generate the expression plasmid, pMttHBGprM80EBundle. The identity of the pMttHBGprM80EBundle clone was confirmed by restriction digestion and limited sequence analysis.

As described above however, the pMttHBGD2prM2X80E used as backbone for this construct lacks the SV40 polyadenylation sequence. Therefore, the BglII/SalI fragment from pMttHBGD2prM2X80EBundle, encoding prM80%E Bundle, was removed from the pMttHBGD2prM2X80EBundle plasmid and cloned into the BglII/XhoI digested pMtt-Xho vector to restore the downstream polyadenylation signal (FIG. 8). The resulting plasmid, pMttHBGD2prM2X80EBundle, was confirmed by restriction digestion and sequence analysis and used to transfect Drosophila cells for expression studies.

Oligonucleotide Sequences:(DNA:SEQ ID NO:31, AA:SEQ ID NO:32, DNA-complementary strand:SEQ ID NO:33)

```
5'GTACCGGCGGTGGCTCCGGCGGTGGCTCCCCCCGCATGAAGCAGCTGGAGGACAAGGTGGAGGA
3'    GCCGCCACCGAGGCCGCCACCGAGGGGGGCGTACTTCGTCGACCTCCTGTTCCACCTCCT
a.a.  T  G  G  G  S  G  G  G  S  P  R  M  K  Q  L  E  D  K  V  E  E

GCTGCTGTCCAAGAACTACCACCTGGAGAACGAGGTGGCCCGCCTGAAGAAGCTGGTGGGCGAGCG
CGACGACAGGTTCTTCATGGTGGACCTCTTGCTCCACCGGGCGGACTTCTTCGACCACCCGCTCGC
   L  L  S  K  N  Y  H  L  E  N  E  V  A  R  L  K  K  L  V  G  E  R

CGGCGGTTGCGGCGGTTAATAGG 3'
GCCGCCAACGCCGCCAATTATCCAGCT 5'
  G  G  C  G  G
```

```
5'GTACCGGCGGTGGCTCCGGCGGTGGCTCCCCCGGCGAGCTGGAGGAGCTGCTGAAGCAC
3'    GCCGCCACCGAGGCCGCCACCGAGGGGGCCGCTCGACCTCCTCGACGACTTCGTG
a.a.  T  G  G  G  S  G  G  G  S  P  G  E  L  E  E  L  L  K  H

CTGAAGGAGCTGCTGAAGGGCCCCCGCAAGGGCGAGCTGGAGGAGCTGCTGAAGCACCT
GACTTCCTCGACGACTTCCCGGGGGCGTTCCCGCTCGACCTCCTCGACGACTTCGTGGA
```

```
                    -continued
L  K  E  L  L  K  G  P  R  K  G  E  L  E  E  L  L  K  H  L GAAGGAGCTGCTGAAGGGCGAGTTCTAATAGG 3'
CTTCCTCGACGACTTCCCGCTCAAGATTATCCAGCT 5'
   K  E  L  L  K  G  E  F
```

EXAMPLE 5

Expression and Secretion of Linked 80%E Dimer, 80%E ZipperI, 80%E ZipperII, and 80%E Bundle from *Drosophila melanogaster* S2 cells

*Drosophila melanogaster* Schneider-2 cells (S2; ATCC, Rockville, Md.) were cotransfected with each of the expression plasmids described in detail above (pMttD2prM2X80Ef, pMttD2prM80EZipperI, pMttD2prM80EZipperII, or pMttD2prM80EBundle) and the selection plasmid, pCoHygro, at a weight ratio of 20:1 using the calcium phosphate coprecipitation method (Wigler et al., 1979; Gibco BRL, Grand Island, N.Y.). The pCoHygro selection plasmid (van der Straten et al., 1989; Smith-Kline Beecham) encodes the *E. coli* hygromycin B phosphotransferase gene under the transcriptional control of the *D. melanogaster* copia transposable element long terminal repeat and confers resistance to hygromycin B. Transfectants were selected for outgrowth in Schneider's medium (Gibco BRL) supplemented with 10% fetal bovine serum (FBS; Hyclone) and 300 μg/ml hygromycin B (Boerhinger-Mannheim). Following significant outgrowth, transfectants were plated at a cell density of $2 \times 10^6$ cell/ml in serum-free IPL-41 medium supplemented with lipids, yeastolate, and Pluronic F68 (Gibco BRL) and induced with 200 μM $CuSO_4$. The media were harvested after 7 days of induction.

Figures 9A, 9B:
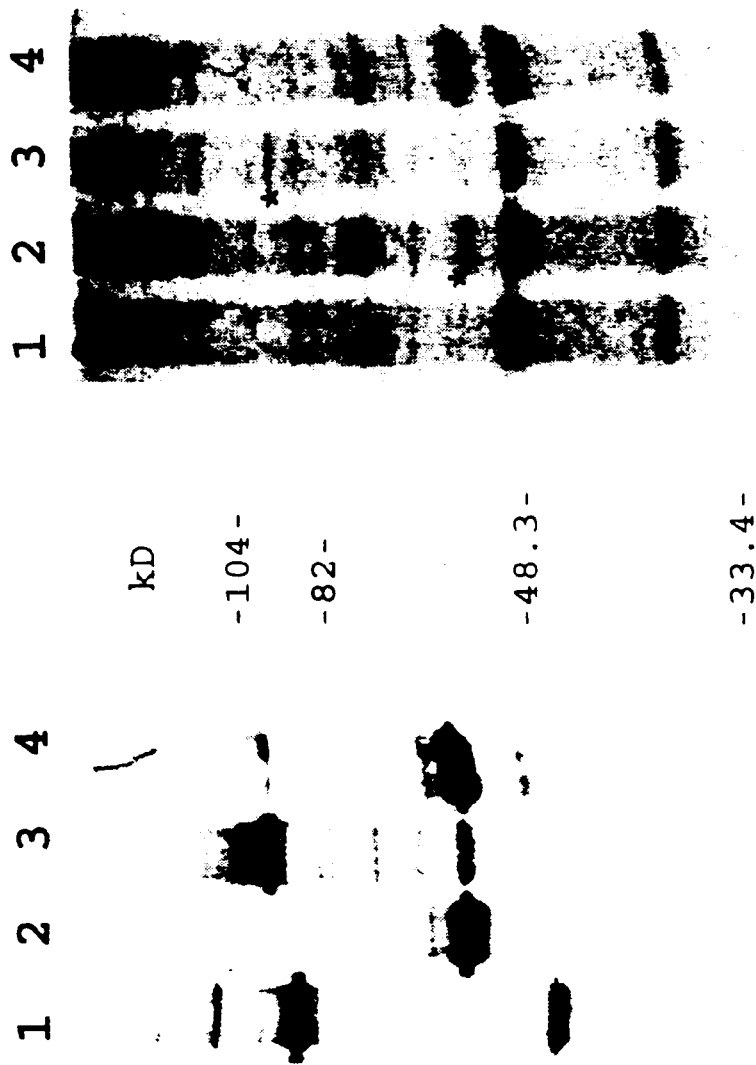
FIGS. 9A–9B show the SDS-PAGE analysis of the expressed dimeric 80% E products secreted from transfected S2 cells.

Proteins secreted into the culture medium were separated by SDS-PAGE, and analyzed by Coomassie blue staining and immunoprobing of Western blots with a polyclonal anti-DEN2 domain B (domain B corresponds to amino acids 296–395 of E). Under non-reducing conditions the expected sizes for Linked 80%E Dimer (lane 1), 80%E ZipperI (lane 2), 80%E ZipperII (lane 3), and 80%E Bundle (lane 4) are 89.1 kD, 99.5 kD, and 49.5 kD, respectively (FIGS. 9A and 9B). An immunoreactive band of appropriate molecular weight was detected in culture medium from all four constructs (FIG. 9A). This analysis confirms that 80%E ZipperII, which was designed with cysteine residues near the carboxy terminal end of the leucine zipper alpha helices to facilitate disulfide bond formation, is covalently dimerized by the disulfide bond. This is in contrast to the non-covalently associated 80%E ZipperI and 80%E Bundle products which migrate as monomers under denaturing but non-reducing conditions. Coomassie blue staining of the crude media reveals a unique band which is plainly visible in the 80%E ZipperI, 80%E ZipperII, and 80%E Bundle lanes (FIG. 9B). Comigrating bands of similar size make visualization of the Linked 80%E Dimer band more difficult. Based upon staining of protein standards we estimate the concentrations of the dimeric proteins to be between 5 and 15 μg/ml depending on the construct and the growth conditions. Thus all four dimeric 80%E proteins are expressed to high levels and efficiently secreted from transfected Drosophila S2 cultures.

EXAMPLE 6

Secreted Dimeric 80%E Products are Glycosylated

Native dengue viral E is a glycoprotein displaying a complex pattern of glycosylation typical of mammalian- and insect cell-expressed proteins. Additional analyses of the secreted recombinant dimeric 80%E products demonstrated that all four of the products are glycosylated Crude media containing Linked 80%E Dimer, 80%E ZipperI, or 80%E Bundle or purified 80%E ZipperII were denatured upon heat treatment with SDS and 2-mercaptoethanol prior to digestion with endoglycosidase H (EndoH) or peptide:N-glycosidase F (PNGase F), as shown in FIGS. 10A and 10B ((–) indicates treatment with no enzyme). Digested and undigested control preparations were separated on SDS-PAGE gels and analyzed by Coomassie blue staining (FIG. 10B) or Western blot analysis (FIG. 10A). Western blots probed with polyclonal anti-DEN2 hyperimmune mouse ascites fluid (HMAF) demonstrate that all dimeric products are resistant to EndoH digestion but sensitive to PNGase F digestion consistent with a complex pattern of glycosylation. Thus, the glycosylation pattern of all four recombinant dimeric 80%E products is similar to that of native dengue E. In addition, this blot demonstrates that under reducing conditions, 80E% ZipperII runs as a monomer similar in size to 80%E ZipperI and 80%E Bundle. This is again consistent with formation of a disulfide bond between the cysteines located near the carboxy-terminal end of the leucine zipper helices.

EXAMPLE 7

Recombinant Dimeric 80%E Products are Recognized by Conformationally-Sensitive Monoclonal Antibodies The reactivity of the recombinant dimeric 80%E products with conformationally-sensitive monoclonal antibodies (MAbs) was assessed using indirect immunofluorescence assays (IFA). Transfected S2 cells were plated onto slides and fixed with ice-cold acetone. The cells were then treated with various polyclonal and monoclonal antibodies diluted with PBS containing 20% FBS. After washing away unbound antibody, bound antibody was detected by reacting the cells with fluorescein isothiocyanate-labeled goat anti-mouse immunoglobulin and observing on a fluorescent microscope after excitation at 470 nm. Cells transfected with the Linked 80%E Dimer, 80%E Bundle, 80%EZipperI, and 80%E ZipperII were efficiently recognized by the conformationally sensitive MAbs 9D12 and 4G2 (Henchal et al., 1992; Mason et al., 1989). In addition all transfectants were recognized by MAb 5A2 which binds to a linear epitope located in the domain B region of E (Megret et al., 1992). These data suggest that these recombinant, dimeric products are antigenically similar to native viral E and therefore may serve as a useful vaccine immunogen.

EXAMPLE 8

Induction of Dengue Virus Neutralizing Antibodies upon Immunization of Mice with Secreted Dimeric 80%E Produced by Transfected S2 Cells S2 cells expressing Linked 80%E Dimer, 80%E Bundle, 80%E ZipperI, and 80%E ZipperII were cultured in serum-free medium (supplemented IPL-41; Gibco BRL) and induced by addition of CuSO$_4$ to a final concentration of 0.2 mM in the culture medium (see example 5 for more detail on culture conditions). The cells were maintained in inducing medium for seven days prior to harvesting. The cells were removed by centrifugation at 1000×G in a Beckman TJ-6 refrigerated centrifuge and the media were filtered through a 0.2 μm cellulose acetate filter (Nalgene). The media containing the recombinant dimeric 80%E products were concentrated approximately ten fold and buffer-exchanged with PBS. The total protein concentration of the medium was determined using a dye binding assay (Biorad). Balb/c mice (Jackson Laboratories) were immunized intraperitoneally with 100 μg total protein of each concentrated medium (of which only ~5–10% was the dengue protein) in Freund's complete adjuvant. The mice were boosted twice, at two week intervals, with 50 μg of each medium in Freund's imcomplete adjuvant. Ten days following the last boost the animals were sacrificed and their blood obtained for testing.

The sera from the immunized mice were tested for the presence of antibodies which bind to recombinant DEN-2 80%E using an indirect ELISA assay. Briefly, plates were coated with purified, recombinant DEN-2 80%E, blocked with bovine serum albumin (BSA), and serial dilutions of the mouse sera were then incubated with the coating antigen. Alkaline phosphatase-labeled goat anti-mouse IgG was used as the secondary detecting antibody, and the color development upon addition of an alkaline phosphatase chromogenic substrate was monitored. The ELISA titer is the reciprocal of the highest dilution of serum which resulted in an optical density two-fold above background (reactivity of the serum against BSA only).

The sera were also tested for virus neutralizing antibodies using a plaque reduction neutralization test (PRNT). In the PRNT assay, the mouse sera were serially diluted with Eagles minimal essential medium (EMEM; Bio Whittaker) supplemented with 10% FBS (Hyclone) and mixed with 100 plaque forming units of Vero-adapted DEN-2 virus (from Robert Putnak, WRAIR). After allowing one hour for neutralization of the virus, the mixtures were plated onto susceptible monkey kidney monolayers (Vero cells, from Robert Putnak, WRAIR) plated in EMEM containing 10% FBS in 6 well tissue culture dishes (Costar). After allowing two hours for the virus to bind, the cells were overlaid with 0.9% agarose (Fisher) in EMEM supplemented with 5% FBS. Viral cytopathic effect was allowed to develop for 6–7 days and the viral plaques were stained with 0.012% neutral red (Sigma) in 1% agarose. The number of plaques in each cluster were counted and compared to a no-serum viral control. The PRNT$_{80}$ titer was the reciprocal of the highest dilution of serum which resulted in at least 80% reduction in the number of plaques compared to the no-serum viral control. Results from the ELISA and PRNT assays are summarized in Table 1. All of the media induced a virus-binding and neutralizing response in the mice demonstrating that all of the dimeric 80%E immunogens are capable of functioning as efficient immunogens.

TABLE 1

Induction of Anti-DEN-2 Immune Response in Mice Immunized with Crude Media Containing Dimeric 80%E Products

| Mouse Number | Immunogen | ELISA Titer | PRNT$_{80}$ Titer |
| --- | --- | --- | --- |
| 179-1 | Linked 80%E Dimer | 25,600 | 800 |
| 179-2 | crude medium | 1600 | 10 |
| 179-3 | 100 μg | 6400 | 1000 |
| 179-4 | Freund's adjuvant | 6400 | 400 |
| 179-5 | | 25,600 | 4000 |
| 180-1 | 80%E Bundle | 1600 | 1000 |
| 180-2 | crude medium | 6400 | 400 |
| 180-3 | 100 μg | 6400 | 400 |
| 180-4 | Freund's adjuvant | 1600 | 200 |
| 180-5 | | 6400 | 4000 |
| 181-1 | 80%E ZipperI | 25,600 | 8000 |
| 181-2 | crude medium | 6400 | 200 |
| 181-3 | 100 μg | 6400 | 2000 |
| 181-4 | Freund's adjuvant | 6400 | 2000 |
| 181-5 | | 1600 | 200 |
| 182-1 | 80%E ZipperII | 25,600 | 800 |
| 182-2 | crude medium | 1600 | 100 |
| 182-3 | 100 μg | 400 | 100 |
| 182-4 | Freund's adjuvant | 1600 | 200 |
| 182-5 | | 6400 | 1000 |
| 177-1 | PBS | <100 | <10 |
| 177-2 | Iscomatrix | <100 | <10 |
| 177-3 | Adjuvant | <100 | <10 |
| 177-4 | | <100 | <10 |
| 177-5 | | <100 | <10 |

EXAMPLE 9

The Secreted, Recombinant Dimeric 80%E Products can be Efficiently Purified Using Immunoaffinity Chromatography The conformationally sensitive MAb 9D12 has been previously used in our laboratory to efficiently purify monomeric DEN-2 80%E. This MAb binds to a conformational epitope in the domain B region (amino acids 296–395) of DEN-2 E. MAb 9D12 was covalently coupled to a HiTrap column (Pharmacia) and used to immunoaffinity-purify each of the recombinant dimeric 80%E molecules, Linked 80%E Dimer, 80%E ZipperI, 80%E ZipperII, and 80%E Bundle. Crude media containing the products was applied to the column and unbound material removed by extensive washing with phosphate-buffered saline (PBS). Bound material was eluted with 0.1 M Glycine HCl pH 2.5 and immediately neutralized with 1.0 M Phosphate pH 7.4. The products were concentrated and buffer exchanged into PBS prior to analysis on SDS-PAGE gels. Each of the products was efficiently purified using this column. Crude media containing the products, flow through concentrated 10-fold, and the purified products were separated on reducing SDS-PAGE gels and detected by immunoprobing (FIG. 11A) or Coomassie blue staining (FIG. 11B). Lanes indicate: 1) 80%E Bundle medium; 2) 80%E Bundle flow through; 3) purified 80%E Bundle; 4) Linked 80%E Dimer flow through; 5) purified Linked 80%E Dimer; 6) 80%E ZipperI medium; 7) 80%E ZipperI flow through; 8) purified 80%E ZipperI; 9) 80%E ZipperII medium; 10) 80%E ZipperII flow through; 11) purified 80%E ZipperII. In all cases the vast majority of the dimeric 80%E bound to the column and was efficiently eluted in a relatively small volume. Thus, this method offers an efficient means of generating purified dimeric 80%E products for animal testing.

EXAMPLE 10

Induction of High Titer Dengue Virus-Neutralizing Antibodies upon Immunization of Mice with Purified, Secreted Dimeric 80%E Culture media from S2 cells expressing Linked 80%E Dimer, 80%E Bundle, 80%E ZipperI, and 80%E ZipperII, prepared as described in Example 8, were used as a source of antigen for additional mouse immunization studies. Each of the products was purified using immunoaffinity chromatography (IAC) as described in Example 9.

Purified Linked 80%E Dimer, 80%E ZipperI, 80%E ZipperII, and 80%E Bundle products were assayed using a quantitative Sandwich ELISA assay, SDS-PAGE analysis, and Western blotting. In the Sandwich ELISA assay MAb 9D12 was coated onto the plates, which were then blocked with BSA. Serial dilutions of a quantitated DEN-2 domain B standard or the products to be assayed were applied in triplicate to each well. Bound antigen was detected using a polyclonal rabbit anti-DEN-2 domain B antibody and horseradish peroxidase-conjugated anti-rabbit immunoglobulin. Chromogenic substrate for the horseradish peroxidase was added and the color development monitored. The absorbance generated by the test antigen was compared to the standard curve and the amount of antigen present in domain B equivalents is determined. To convert from domain B equivalents to dimeric 80%E, the weight ratio (~4.5 for most of the products), determined by comparing the relative molecular weight of the dimeric 80%E to domain B and dividing by the number of domain B regions present in the dimeric 80%E product, was used. Each purified dimeric product was quantitated using this assay for mouse immunizations.

Balb/c mice (Jackson Laboratories) were immunized with 1 µg of each purified, secreted dimeric 80%E product. The immunizations were given subcutaneously using Iscomatrix (Iscotech) adjuvant. Two immunizations were given at 4 week intervals. Ten days following the final immunization the mice were sacrificed and their sera tested for virus binding and neutralizing antibodies by ELISA and PRNT as described in example 8. The results are summarized in Table 2. As is clearly evident, all of the dimeric 80%E products induced a high-titer virus neutralizing response. These titers are higher than any titers previously reported in the literature and suggest that these dimeric 80%E products are exceptionally effective vaccine candidates.

TABLE 2

Induction of Anti-DEN-2 Immune Response in Mice Immunized with Purified Recombinant Dimeric 80%E Products

| Mouse Number | Immunogen | ELISA Titer | PRNT$_{80}$ Titer |
|---|---|---|---|
| 173-1 | IAC-pure | 102,400 | 4000 |
| 173-2 | Linked 80%E Dimer | 102,400 | 8000 |
| 173-3 | 1 µg | 102,400 | 8000 |
| 173-4 | Iscomatrix | 102,400 | 4000 |
| 173-5 | Adjuvant | 102,400 | 4000 |
| 185-1 | IAC-pure | 102,400 | 32,000 |
| 185-2 | 80%E Bundle | 25,600 | 4000 |
| 185-3 | 1 µg | 25,600 | 4000 |
| 185-4 | Iscomatrix | 25,600 | 16,000 |
| 185-5 | Adjuvant | 102,400 | 2000 |
| 174-1 | IAC-pure | 6400 | 200 |
| 174-2 | 80%E ZipperI | 409,600 | 4000 |
| 174-3 | 1 µg | 102,400 | 8000 |
| 174-4 | Iscomatrix | 102,400 | 16,000 |
| 174-5 | Adjuvant | 102,400 | 8000 |
| 175-1 | IAC-pure | 102,400 | 8000 |
| 175-2 | 80%E ZipperII | 25,600 | 2000 |
| 175-3 | 1 µg | 102,400 | 16,000 |
| 175-4 | Iscomatrix | 102,400 | 8000 |
| 175-5 | Adjuvant | 102,400 | 4000 |
| 176-1 | IAC-pure | 102,400 | 4000 |
| 176-2 | 80%E | 102,400 | 16,000 |
| 176-3 | 1 µg | 25,600 | 8000 |
| 176-4 | Iscomatrix | 25,600 | 4000 |

TABLE 2-continued

Induction of Anti-DEN-2 Immune Response in Mice Immunized with Purified Recombinant Dimeric 80%E Products

| Mouse Number | Immunogen | ELISA Titer | PRNT$_{80}$ Titer |
|---|---|---|---|
| 176-5 | Adjuvant | 102,400 | 4000 |
| 177-1 | PBS | <100 | <10 |
| 177-2 | Iscomatrix | <100 | <10 |
| 177-3 | Adjuvant | <100 | <10 |
| 177-4 |  | <100 | <10 |
| 177-5 |  | <100 | <10 |

EXAMPLE 11

Dose Response of Mice Immunized with Purified, Secreted Recombinant Dimeric Dengue 2 Virus Proteins Culture media from S2 cells expressing dengue 2 virus (DEN-2) 80%E monomer, Linked 80%E Dimer, DEN-2 80%E Bundle, and Den-2 80%E ZipperII were used as source for the antigens. Each of the products was purified using immunoaffinity chromatography as described in Example 9. The products were quantitated by ultraviolet spectroscopy. Balb/c mice were immunized by subcutaneous injection with 10, 1, or 0.2 µg of the respective recombinant products in 10 µg Iscomatrix adjuvant (Iscotech). Two immunizations were given at 4 week intervals. Ten days following the final immunization the mice were sacrificed and their sera tested for virus neutralizing antibodies by PRNT test. The results are summarized in Table 3. As is clearly evident, all of the recombinant products induced a high-titer virus neutralizing response even at very low antigen doses. No statistically significant difference could be detected between the groups.

TABLE 3

Induction of Anti-DEN-2 Immune Response in Mice Immunized with Purified Recombinant Dimeric or Monomeric 80%E Products Geometric Mean of PRNT$_{80}$ Titer

| Antigen | 10 µg Dose | 1 µg Dose | 0.2 µg Dose |
|---|---|---|---|
| DEN-2 Linked 80%E Dimer | 6355 | 2828 | 2766 |
| DEN-2 80%E ZipperII | 6498 | 3732 | 1206 |
| DEN-2 80%E Bundle | 9190 | 3482 | 777 |
| DEN-2 80%E Monomer | 10,556 | 3031 | 1293 |

EXAMPLE 12

Dimeric and Monomeric DEN-2 Recombinant 80%E Proteins Induce a Protective Response in Suckling Mice Ten to 13 day old Balb/c mice were immunized by subcutaneous injection with either 1 or 5 µg or immunoaffinity purified recombinant DEN-2 80%E monomer, Linked 80%E Dimer, 80%E ZipperII, or 80%E Bundle in 2 µg IscoMatrix. A second equivalent dose was administered two weeks later. One week following the final dose the mice were challenged by intracranial injection with 100 LD$_{50}$ of DEN-2 virus New Guinea C strain adapted for growth in mice. Morbidity and mortality was monitored for 17 days post-challenge. The results are summarized in FIG. 12. All immunogens, at both 1 and 5 μg doses, resulted in complete protection of the suckling mice, demonstrating that the dimeric antigens induce potent protective responses in mice.

EXAMPLE 13

Dimeric DEN-2 Antigens Induce Virus Neutralizing and Protective Responses in Primates Groups of three rhesus monkeys were immunized with three doses of 30 μg each of immunoaffinity purified DEN-2 80%E monomer, Linked 80%E Dimer, 80%E ZipperII, or 80%E Bundle in 50 μg IscoMatrix adjuvant. The doses were administered subcutaneously on day 0, day 34, and day 120 of the study. Approximately one month following the final vaccination the monkeys were challenged by subcutaneous injection with $10^4$ pfu of live DEN-2 virus (strain S16803). Control animals included animals inoculated with live-attenuated DEN-2 Virus (PDK-50) or saline. Neutralizing antibody responses were monitored throughout the course of the experiment and are summarized in Table 4 below. In addition, protection from viral replication post-challenge was monitored by determining the level of virus in the blood for eleven days post-challenge. The results of the viremia assays are summarized in Table 5 below. In all cases a potent virus neutralizing response was induced by the vaccination schedule. In addition, significant protection from viral challenge compared to monkeys immunized with saline was observed in all monkeys except one (FEV).

TABLE 4

Virus neutralizing Response in Monkeys Immunized with Recombinant DEN-2 80%E Dimers and Monomer

| Monkey ID | Immunogen | Day 0 Vaccine | Day 15 | Day 34 Vaccine | Day 64 | Day 90 | Day 120 Vaccine | Day 153 Challenge | Day 184 |
|---|---|---|---|---|---|---|---|---|---|
| FEV | 30 μg DEN-2 | <10 | 70 | 80 | 640 | 200 | 145 | 720 | 11,660 |
| FKB | Linked 80%E | <10 | 60 | 40 | 1230 | 460 | 415 | 6310 | 44,100 |
| EKH | Dimer Iscomatrix | <10 | <10 | 55 | 1670 | 270 | 250 | 4060 | 14,310 |
| FJP | 30 μg DEN-2 | <10 | 10 | <10 | 950 | 260 | 120 | 3690 | 57,690 |
| GPC | 80%E | <10 | <10 | <10 | 630 | 205 | 130 | 3100 | 23,265 |
| HTX | Monomer Iscomatrix | <10 | <10 | <10 | 540 | 160 | 150 | 1680 | 1290 |
| HTB | 30 μg DEN-2 | <10 | <10 | 30 | 950 | 150 | 130 | 3350 | 53,430 |
| HTH | 80%E ZipperII | <10 | 10 | 40 | 1180 | 250 | 180 | 3415 | 31,625 |
| HPF | Iscomatrix | <10 | 115 | 20 | 215 | 105 | 110 | 1525 | 11,810 |
| HTF | 30 μg DEN-2 | <10 | <10 | 15 | 70 | 80 | 90 | 2415 | 22,105 |
| GHF | 80%E Bundle | <10 | 10 | 95 | 1850 | 1110 | 665 | 10,595 | 18,835 |
| GXD | Iscomatrix | <10 | 15 | 25 | 215 | 85 | 70 | 1060 | 16,260 |
| GJK | Saline | <10 | <10 | <10 | <10 | <10 | <10 | <10 | 380 |
| HVA | Iscomatrix | <10 | <10 | <10 | <10 | <10 | <10 | <10 | 1080 |
| FEB | | <10 | <10 | <10 | <10 | <10 | <10 | <10 | 2510 |
| GXJ | DEN-2 | <10 | 975 | 310 | 190 | 245 | 310 | 310 | 415 |
| HCG | PDK-50 | <10 | 40 | 70 | 155 | 145 | 100 | 75 | 1180 |
| GEG | Vaccine | <10 | 65 | 5110 | 975 | 1450 | 1800 | 1600 | 1825 |

TABLE 5

Viremia in Vaccinated Monkeys Post-Challenge with Live DEN-2 Virus

| Vaccine | Animal | Viremic Days | | | | | | | | | | |
|---|---|---|---|---|---|---|---|---|---|---|---|---|
| | | 1 | 2 | 3 | 4 | 5 | 6 | 7 | 8 | 9 | 10 | 11 |
| 30 μg DEN-2 Linked 80%E | FEV | 0 | 0 | 0 | F | F | + | + | F | 0 | 0 | 0 |
| | FKB | 0 | 0 | 0 | 0 | 0 | 0 | + | 0 | 0 | 0 | 0 |
| | EKH | 0 | 0 | 0 | 0 | 0 | 0 | 0 | 0 | 0 | 0 | 0 |

TABLE 5-continued

Viremia in Vaccinated Monkeys Post-Challenge with Live DEN-2 Virus

| Vaccine | Animal | Viremic Days | | | | | | | | | | |
|---|---|---|---|---|---|---|---|---|---|---|---|---|
| | | 1 | 2 | 3 | 4 | 5 | 6 | 7 | 8 | 9 | 10 | 11 |
| Dimer Iscomatrix 30 μg DEN-2 80%E Monomer Iscomatrix | FJP | 0 | 0 | 0 | 0 | + | F | + | 0 | 0 | 0 | 0 |
| | GPC | 0 | 0 | 0 | 0 | F | + | + | 0 | 0 | 0 | 0 |
| | HTX | 0 | 0 | 0 | 0 | 0 | 0 | 0 | 0 | 0 | 0 | 0 |
| 30 μg DEN-2 80%E ZipperII Iscomatrix | HTB | 0 | 0 | 0 | 0 | 0 | 0 | + | 0 | 0 | 0 | 0 |
| | HTH | 0 | 0 | 0 | 0 | 0 | 0 | 0 | 0 | 0 | 0 | 0 |
| | HPF | 0 | 0 | 0 | 0 | + | + | + | 0 | 0 | 0 | 0 |
| 30 μg DEN-2 80%E Bundle Iscomatrix | HTF | 0 | 0 | 0 | 0 | 0 | 0 | 0 | 0 | 0 | 0 | 0 |
| | GHF | 0 | 0 | 0 | 0 | 0 | + | + | 0 | 0 | 0 | 0 |
| | GXD | 0 | 0 | 0 | 0 | 0 | 0 | 0 | F | + | + | 0 |
| Saline Iscomatrix | GJK | + | + | + | + | + | + | 0 | 0 | 0 | 0 | 0 |
| | HVA | 0 | 0 | + | + | + | + | + | + | 0 | 0 | 0 |
| | FEB | 0 | + | + | + | + | + | F | 0 | 0 | 0 | 0 |
| DEN-2 PDK-50 Vaccine | GXJ | 0 | + | + | 0 | 0 | 0 | 0 | 0 | 0 | 0 | 0 |
| | HCG | 0 | 0 | 0 | 0 | 0 | 0 | 0 | 0 | 0 | 0 | 0 |
| | GEG | 0 | 0 | 0 | 0 | 0 | 0 | 0 | 0 | 0 | 0 | 0 |

0 = no plaques
+ = >10 plaques
F = <10 plaques

EXAMPLE 14

Construction and Expression of Dimeric Form of Dengue 4 80%

While the DEN-2 80%E monomer and dimer forms are both very potent immunogens, the monomeric form of DEN-4 80%E is a much less potent immunogen. Therefore, a dimeric form (ZipperII form) of DEN-4 80%E was constructed to examine whether the dimeric form exhibits enhanced immunogenicity. To construct the ZipperII form, the plasmid pMttD4prM80Ef.3+G.13, which encodes full-length prM and first 395 amino acids of DEN-4 E, and pMttD2prM80E ZipperII which encodes full-length prM, the first 395 amino acids of DEN-2 E, the flexible linker and ZipperII sequence described in detail in Example 3 were used as templates. The 3'end of DEN-4 80%E was PCR amplified from the pMttD4prM80Ef.3+G.13 template using an internal DEN-4 primer (P48D4E1435p; 5'-CCAGGTCACCATGGGTAG) (SEQ ID NO:34), corresponding to nucleotides 1435–1452 of DEN-4, as positive strand primer and a negative strand primer which corresponds to the last amino acids of DEN-4 80%E and then continues in frame to contain the 5' end of the flexible linker up to and including the KpnI site (P64D4ZII-M; 5'-ACCACCACCACCAGAACCACCACCCCCTTTCCT-GAACCAATGGAGTG) (SEQ ID NO:35). The 3' portion of the flexible linker (up to and including the KpnI site) and the ZipperII sequence were PCR amplified from the pMttD2prM80E ZipperII template using the positive strand primer P64D4ZII-P (5'-TCAGGAAAGGGGGTGGTGGTTCTGGTG-GTGGTGGTTCTGGT GGTGGTACC) (SEQ ID NO:36) and the negative strand primer which binds within the pMttΔXho vector downstream of the SalI site (P64MTT1084-M; 50'-ATACCGCAAGCGACAGGCCG) (SEQ ID NO:37). The resultant PCR product contains the second half of the linker (including the KpnI site), the ZipperII sequence, the stop codons at the end of the ZipperII sequence, and the pMttΔXho sequence including the SV40 polyadenylation signal up to the SalI site.

The two PCR products contain an overlap which was utilized in an overlap extension reaction to generate a single product of full-length. Briefly, the two PCR products were mixed together, heated and allowed to anneal to each other. Ten cycles of heating and slow annealing in the presence of Taq DNA polymerase were conducted. Primers P48D4E1435p and P64MTT1084-M (positive strand primer from the DEN-4 80%E reaction with the minus strand primer from the ZipperII reaction) were then added and standard PCR amplification conducted. The full-length product was digested with SacI and SalI and ligated into pMttD4prM80Ef.3+G13 digested with SacI and SalI. Plasmid DNA from two independent bacterial transformants, pMttD4prM80EZipII.1 and pMttD4prM80EZippII.2, was confirmed by restriction digestion and limited sequence analysis.

The expression plasmids were cotransfected into S2 cells using the calcium phosphate coprecipitation method (Wigler et al., 1979; Gibco BRL, Grand Island, N.Y.). The pCoHygro selection plasmid encodes the *E. coli* hygromycin B phosphotransferase gene under the transcriptional control of the copia transposable element long terminal repeat. Transfectants were selected for outgrowth in Schneider's medium (Gibco BRL) supplemented with 10% fetal bovine serum (Hyclone) and 300 µg/ml hygromycin B (Boerhinger Mannheim). Following significant outgrowth, transfectants were plated at a density of $2\times10^6$ cells/ml in serum-free IPL-41 medium supplemented with lipids, yeastolate, and Pluronice F68 (Gibco BRL) and expression induced with 200 µM $CuSO_4$. The media were harvested after 7 days of induction. Analysis of the culture media on SDS-PAGE gels revealed secretion levels ranging from 5–10 mg/L of DEN-4 80%E ZipperII. The recombinant DEN-4 80%E ZipperII product was purified from the culture medium using immunoaffinity chromatography as described in detail in Example 9 except that the conformationally sensitive monoclonal antibody 4G2 was used in place of 9D12.

EXAMPLE 15

DEN-4 80%E ZipperII Induces a Potent Virus Neutralizing Response in Mice

Groups of 10 each adult Balb/c mice were immunized with various doses of immunoaffinity purified DEN-4 80%E monomer or dimeric DEN-4 80%E ZipperII. Doses of 30, 10, 3, 1, or 0.3 µg were administered by subcutaneous injection with 10 µg IscoMatrix adjuvant. A second equivalent dose was administered 4 weeks later. Ten days following the second dose the animals were sacrificed and the virus neutralizing antibody response assayed. The results are summarized in Table 6. The immunogenic superiority of the dimeric DEN-4 80%E ZipperII antigen compared to the DEN-4 80%E monomer is clearly evident from this study.

TABLE 6

Virus Neutralizing Antibody Response Induced by Monomeric and Dimeric DEN-4 80%E Antigens

| Dose of Antigen (µg) | Geometric Mean $PRNT_{50}$ Titer DEN-4 80%E Monomer | Geometric Mean $PRNT_{50}$ Titer DEN-4 80%E ZipperII |
|---|---|---|
| 30 | 728 | 1400 |
| 10 | 526 | 1609 |
| 3 | 278 | 1613 |
| 1 | 144 | 1472 |
| 0.3 | 28 | 1251 |

What is claimed is:

1. A vaccine that generates a protective, neutralizing antibody response to a Flavivirus in a murine host, wherein said vaccine comprises a therapeutically effective amount of a dimeric 80%E, said dimeric 80%E having been secreted as a recombinantly produced protein from Drosophila Schneider cells, wherein 80%E represents the N-terminal 80% portion of the protein from residue 1 to residue 395.

2. The vaccine of claim 1 wherein said dimeric 80%E is selected from the group consisting of: linked 80%E dimer; 80%E ZipperI; 80%E ZipperII; and 80%E Bundle.

3. The vaccine of claim 2 wherein the linked 80%E dimer is a truncated envelope protein of serotype DEN-1.

4. The vaccine of claim 2 wherein the linked 80%E dimer is a truncated envelope protein of serotype DEN-2.

5. The vaccine of claim 1 wherein the linked 80%E dimer is a truncated envelope protein of serotype DEN-3.

6. The vaccine of claim 1 wherein the linked 80%E dimer is a truncated envelope protein of serotype DEN-4.

7. A multivalent vaccine that generates a protective, neutralizing antibody response to a Flavivirus in a murine host, wherein said vaccine comprises a therapeutically effective amount of a first dimeric 80%E product of one flaviviral serotype; a second dimeric 80%E product of a second flaviviral serotype; a third dimeric 80%E product of a third flaviral serotype; and a fourth dimeric 80%E product of a fourth flaviviral serotype; wherein all dimeric 80%E products have been secreted as recombinantly produced protein from a Drosophila Schneider cell, wherein 80%E is the N-terminal 80% of the protein from residue 1 to 395.

8. The vaccine of claim 7 wherein said dimeric 80%E products are envelope proteins of serotypes selected from the group consisting of: DEN-1; DEN-2; DEN-3; and DEN-4.

9. The vaccine of claim 1 wherein said Flavivirus is a dengue virus.

10. The vaccine of claim 2 wherein said Flavivirus is a dengue virus.

11. The vaccine of claim 7 wherein said Flavivirus is a dengue virus.

12. An immunogenic polypeptide comprising a dimeric 80%E, said dimeric 80%E having been secreted as a recombinantly produced protein from Drosophila Schneider cells, wherein 80%E represents the N-terminal 80% of the protein from residue 1 to residue 395.

13. The immunogenic polypeptide of claim 12 wherein said dimeric 80%E is selected from the group consisting of: linked 80%E dimer, 80%E ZipperI; 80%E ZipperII; and 80%E bundle.

14. The immunogenic polypeptide of claim 13 wherein the linked 80%E dimer is a truncated envelope protein which is at least one member selected from the group consisting of serotype DEN-1, serotype DEN-2, serotype DEN-3, and serotype DEN-4.

15. An immunogenic composition that generates a protective, neutralizing antibody response to a Flavivirus in a murine host, comprising the immunogenic polypeptide defined in claim 12 and a physiologically acceptable carrier.

16. The immunogenic composition defined in claim 15 further comprising an adjuvant.

17. The immunogenic composition defined in claim 15 wherein said adjuvant is Iscomatrix.

18. The immunodiagnostic for the detection of Flavivirus comprising the immunogenic polypeptide defined in claim 12.

19. A multivalent immunodiagnostic for the detection of Flavivirus comprising at least two of the immunogenic polypeptides defined in claim 12 of at least two flaviviral serotypes.

20. An immunodiagnostic kit for the detection of Flavivirus in a test subject comprising
   a) the immunogenic polypeptide defined in claim 12;
   b) a suitable support phase coated with dimeric 80%E; and
   c) labeled antibodies immunoreactive to antibodies from said test subject.

21. An immunodiagnostic kit for the detection of Flavivirus in a test subject comprising
   a) the multivalent immunodiagnostic polypeptide defined in claim 19;
   b) a suitable support phase coated with dimeric 80%E; and
   c) labeled antibodies immunoreactive to antibodies from said test subject.

* * * * *

SEQUENCE LISTING

<160> NUMBER OF SEQ ID NOS: 37

<210> SEQ ID NO 1
<211> LENGTH: 5

```
<212> TYPE: PRT
<213> ORGANISM: Artificial Sequence
<220> FEATURE:
<223> OTHER INFORMATION: Linker

<400> SEQUENCE: 1

Gly Gly Gly Gly Ser
 1               5

<210> SEQ ID NO 2
<211> LENGTH: 3381
<212> TYPE: DNA
<213> ORGANISM: Dengue virus
<220> FEATURE:
<221> NAME/KEY: CDS
<222> LOCATION: (1)...(3381)

<400> SEQUENCE: 2 atg aat aac caa cgg aaa aag gcg aga aac acg cct ttc aat atg ctg      48
Met Asn Asn Gln Arg Lys Lys Ala Arg Asn Thr Pro Phe Asn Met Leu
 1               5                  10                  15 aaa cgc gag aga aac cgc gtg tca act gta caa cag ttg aca aag aga      96
Lys Arg Glu Arg Asn Arg Val Ser Thr Val Gln Gln Leu Thr Lys Arg
             20                  25                  30 ttc tca ctt gga atg ctg cag gga cga gga cca cta aaa ttg ttc atg     144
Phe Ser Leu Gly Met Leu Gln Gly Arg Gly Pro Leu Lys Leu Phe Met
         35                  40                  45 gcc ctg gtg gca ttc ctt cgt ttc cta aca atc cca cca aca gca ggg     192
Ala Leu Val Ala Phe Leu Arg Phe Leu Thr Ile Pro Pro Thr Ala Gly
     50                  55                  60 ata tta aaa aga tgg gga aca att aaa aaa tca aag gct att aat gtt     240
Ile Leu Lys Arg Trp Gly Thr Ile Lys Lys Ser Lys Ala Ile Asn Val
 65                  70                  75                  80 ctg aga ggc ttc agg aaa gag att gga agg atg ctg aat atc tta aac     288
Leu Arg Gly Phe Arg Lys Glu Ile Gly Arg Met Leu Asn Ile Leu Asn
                 85                  90                  95 agg aga cgt aga act gca ggc atg atc atc atg ctg att cca aca gtg     336
Arg Arg Arg Arg Thr Ala Gly Met Ile Ile Met Leu Ile Pro Thr Val
            100                 105                 110 atg gcg ttt cat ctg acc aca cgc aac gga gaa cca cac atg atc gtc     384
Met Ala Phe His Leu Thr Thr Arg Asn Gly Glu Pro His Met Ile Val
        115                 120                 125 agt aga caa gaa aaa ggg aaa agc ctt ctg ttt aag aca aag gac ggc     432
Ser Arg Gln Glu Lys Gly Lys Ser Leu Leu Phe Lys Thr Lys Asp Gly
    130                 135                 140 acg aac atg tgt acc ctc atg gcc atg gac ctt ggt gag ttg tgt gaa     480
Thr Asn Met Cys Thr Leu Met Ala Met Asp Leu Gly Glu Leu Cys Glu
145                 150                 155                 160 gac aca atc acg tat aaa tgt ccc ttt ctc aag cag aac gaa cca gaa     528
Asp Thr Ile Thr Tyr Lys Cys Pro Phe Leu Lys Gln Asn Glu Pro Glu
                165                 170                 175 gac ata gat tgt tgg tgc aac tcc acg tcc aca tgg gta act tat ggg     576
Asp Ile Asp Cys Trp Cys Asn Ser Thr Ser Thr Trp Val Thr Tyr Gly
            180                 185                 190 aca tgt acc acc aca gga gag cac aga aga gaa aaa aga tca gtg gcg     624
Thr Cys Thr Thr Thr Gly Glu His Arg Arg Glu Lys Arg Ser Val Ala
        195                 200                 205 ctt gtt cca cac gtg gga atg gga ttg gag aca cga act gaa aca tgg     672
Leu Val Pro His Val Gly Met Gly Leu Glu Thr Arg Thr Glu Thr Trp
    210                 215                 220 atg tca tca gaa ggg gcc tgg aaa cat gcc cag aga att gaa act tgg     720
Met Ser Ser Glu Gly Ala Trp Lys His Ala Gln Arg Ile Glu Thr Trp
```

```
        225                 230                 235                 240
att ctg aga cat cca ggc ttt acc ata atg gcc gca atc ctg gca tac        768
Ile Leu Arg His Pro Gly Phe Thr Ile Met Ala Ala Ile Leu Ala Tyr
                245                 250                 255 acc ata gga acg acg cat ttc caa aga gtc ctg ata ttc atc cta ctg        816
Thr Ile Gly Thr Thr His Phe Gln Arg Val Leu Ile Phe Ile Leu Leu
            260                 265                 270 aca gcc atc gct cct tca atg aca atg cgc tgc ata gga ata tca aat        864
Thr Ala Ile Ala Pro Ser Met Thr Met Arg Cys Ile Gly Ile Ser Asn
        275                 280                 285 agg gac ttt gtg gaa gga gtg tca gga ggg agt tgg gtt gac ata gtt        912
Arg Asp Phe Val Glu Gly Val Ser Gly Gly Ser Trp Val Asp Ile Val
    290                 295                 300 tta gaa cat gga agt tgt gtg acg acg atg gca aaa aat aaa cca aca        960
Leu Glu His Gly Ser Cys Val Thr Thr Met Ala Lys Asn Lys Pro Thr
305                 310                 315                 320 ctg gac ttt gaa ctg ata aaa aca gaa gcc aaa caa ccc gcc acc tta       1008
Leu Asp Phe Glu Leu Ile Lys Thr Glu Ala Lys Gln Pro Ala Thr Leu
                325                 330                 335 agg aag tac tgt ata gag gct aaa ctg acc aac acg aca aca gac tcg       1056
Arg Lys Tyr Cys Ile Glu Ala Lys Leu Thr Asn Thr Thr Thr Asp Ser
            340                 345                 350 cgc tgc cca aca caa ggg gaa ccc acc ctg aat gaa gag cag gac aaa       1104
Arg Cys Pro Thr Gln Gly Glu Pro Thr Leu Asn Glu Glu Gln Asp Lys
        355                 360                 365 agg ttt gtc tgc aaa cat tcc atg gta gac aga gga tgg gga aat gga       1152
Arg Phe Val Cys Lys His Ser Met Val Asp Arg Gly Trp Gly Asn Gly
    370                 375                 380 tgt gga tta ttt gga aaa gga ggc atc gtg acc tgt gcc atg ttc aca       1200
Cys Gly Leu Phe Gly Lys Gly Gly Ile Val Thr Cys Ala Met Phe Thr
385                 390                 395                 400 tgc aaa aag aac atg gag gga aaa att gtg cag cca gaa aac ctg gaa       1248
Cys Lys Lys Asn Met Glu Gly Lys Ile Val Gln Pro Glu Asn Leu Glu
                405                 410                 415 tac act gtc gtt ata aca cct cat tca ggg gaa gaa cat gca gtc gga       1296
Tyr Thr Val Val Ile Thr Pro His Ser Gly Glu Glu His Ala Val Gly
            420                 425                 430 aat gac aca gga aaa cat ggt aaa gaa gtc aag ata aca cca cag agc       1344
Asn Asp Thr Gly Lys His Gly Lys Glu Val Lys Ile Thr Pro Gln Ser
        435                 440                 445 tcc atc aca gag gcg gaa ctg aca ggc tat ggc act gtt acg atg gag       1392
Ser Ile Thr Glu Ala Glu Leu Thr Gly Tyr Gly Thr Val Thr Met Glu
    450                 455                 460 tgc tct cca aga acg ggc ctc gac ttc aat gag atg gtg ttg ctg caa       1440
Cys Ser Pro Arg Thr Gly Leu Asp Phe Asn Glu Met Val Leu Leu Gln
465                 470                 475                 480 atg aaa gac aaa gct tgg ctg gtg cac aga caa tgg ttc cta gac cta       1488
Met Lys Asp Lys Ala Trp Leu Val His Arg Gln Trp Phe Leu Asp Leu
                485                 490                 495 ccg ttg cca tgg ctg ccc gga gca gac aca caa gga tca aat tgg ata       1536
Pro Leu Pro Trp Leu Pro Gly Ala Asp Thr Gln Gly Ser Asn Trp Ile
            500                 505                 510 cag aaa gag aca ctg gtc acc ttc aaa aat ccc cat gcg aaa aaa cag       1584
Gln Lys Glu Thr Leu Val Thr Phe Lys Asn Pro His Ala Lys Lys Gln
        515                 520                 525 gat gtt gtt gtc tta gga tcc caa gag ggg gcc atg cat aca gca ctc       1632
Asp Val Val Val Leu Gly Ser Gln Glu Gly Ala Met His Thr Ala Leu
    530                 535                 540 aca ggg gct acg gaa atc cag atg tca tca gga aac ctg ctg ttc aca       1680
Thr Gly Ala Thr Glu Ile Gln Met Ser Ser Gly Asn Leu Leu Phe Thr
```

|   |   |   |   |   |   |   |   |   |   |   |   |   |   |   |   |
|---|---|---|---|---|---|---|---|---|---|---|---|---|---|---|---|
| Thr | Gly | Ala | Thr | Glu | Ile | Gln | Met | Ser | Ser | Gly | Asn | Leu | Leu | Phe | Thr |
| 545 |     |     |     | 550 |     |     |     |     | 555 |     |     |     |     | 560 |     |

```
gga cat ctt aag tgc agg ctg aga atg gac aaa tta caa ctt aaa ggg    1728
Gly His Leu Lys Cys Arg Leu Arg Met Asp Lys Leu Gln Leu Lys Gly
            565                 570                 575 atg tca tac tcc atg tgc aca gga aag ttt aaa gtt gtg aag gaa ata    1776
Met Ser Tyr Ser Met Cys Thr Gly Lys Phe Lys Val Val Lys Glu Ile
                580                 585                 590 gca gaa aca caa cat gga aca ata gtc att aga gta caa tat gaa gga    1824
Ala Glu Thr Gln His Gly Thr Ile Val Ile Arg Val Gln Tyr Glu Gly
            595                 600                 605 gac ggc tct cca tgc aag atc cct ttt gag ata atg gat ctg gaa aaa    1872
Asp Gly Ser Pro Cys Lys Ile Pro Phe Glu Ile Met Asp Leu Glu Lys
        610                 615                 620 aga cat gtt ttg ggc cgc ctg atc aca gtc aac cca att gta aca gaa    1920
Arg His Val Leu Gly Arg Leu Ile Thr Val Asn Pro Ile Val Thr Glu
625                 630                 635                 640 aag gac agc cca gtc aac ata gaa gca gaa cct cca ttc gga gac agc    1968
Lys Asp Ser Pro Val Asn Ile Glu Ala Glu Pro Pro Phe Gly Asp Ser
                645                 650                 655 tac atc atc ata gga gtg gaa cca gga caa ttg aag ctg gac tgg ttc    2016
Tyr Ile Ile Ile Gly Val Glu Pro Gly Gln Leu Lys Leu Asp Trp Phe
            660                 665                 670 aag aaa gga agt tcc atc ggc caa atg ttt gag aca aca atg agg gga    2064
Lys Lys Gly Ser Ser Ile Gly Gln Met Phe Glu Thr Thr Met Arg Gly
        675                 680                 685 gcg aaa aga atg gcc att ttg ggc gac aca gcc tgg gat ttt gga tct    2112
Ala Lys Arg Met Ala Ile Leu Gly Asp Thr Ala Trp Asp Phe Gly Ser
690                 695                 700 ctg gga gga gtg ttc aca tca ata gga aag gct ctc cac cag gtt ttt    2160
Leu Gly Gly Val Phe Thr Ser Ile Gly Lys Ala Leu His Gln Val Phe
705                 710                 715                 720 gga gca atc tac ggg gct gct ttc agt ggg gtc tca tgg act atg aag    2208
Gly Ala Ile Tyr Gly Ala Ala Phe Ser Gly Val Ser Trp Thr Met Lys
                725                 730                 735 atc ctc ata gga gtt atc atc aca tgg ata gga atg aac tca cgt agc    2256
Ile Leu Ile Gly Val Ile Ile Thr Trp Ile Gly Met Asn Ser Arg Ser
            740                 745                 750 aca tca ctg tct gtg tca ctg gta tta gtg gga atc gtg aca ctg tac    2304
Thr Ser Leu Ser Val Ser Leu Val Leu Val Gly Ile Val Thr Leu Tyr
        755                 760                 765 ttg gga gtt atg gtg cag gcc gat agt ggt tgc gtt gtg agc tgg aag    2352
Leu Gly Val Met Val Gln Ala Asp Ser Gly Cys Val Val Ser Trp Lys
770                 775                 780 aac aaa gaa cta aaa tgt ggc agt gga ata ttc gtc aca gat aac gtg    2400
Asn Lys Glu Leu Lys Cys Gly Ser Gly Ile Phe Val Thr Asp Asn Val
785                 790                 795                 800 cat aca tgg aca gaa caa tac aag ttc caa cca gaa tcc cct tca aaa    2448
His Thr Trp Thr Glu Gln Tyr Lys Phe Gln Pro Glu Ser Pro Ser Lys
                805                 810                 815 ctg gct tca gcc atc cag aaa gct cat gaa gag ggc atc tgt gga atc    2496
Leu Ala Ser Ala Ile Gln Lys Ala His Glu Glu Gly Ile Cys Gly Ile
            820                 825                 830 cgc tca gta aca aga ctg gaa aat ctt atg tgg aaa caa ata aca tca    2544
Arg Ser Val Thr Arg Leu Glu Asn Leu Met Trp Lys Gln Ile Thr Ser
        835                 840                 845 gaa ttg aat cat att cta tca gaa aat gaa gtg aaa ctg acc atc atg    2592
Glu Leu Asn His Ile Leu Ser Glu Asn Glu Val Lys Leu Thr Ile Met
850                 855                 860
```

```
aca gga gac atc aaa gga atc atg cag gta gga aaa cga tct ctg cgg    2640
Thr Gly Asp Ile Lys Gly Ile Met Gln Val Gly Lys Arg Ser Leu Arg
865             870                 875                 880 cct caa ccc act gag ttg agg tat tca tgg aaa aca tgg ggt aaa gcg    2688
Pro Gln Pro Thr Glu Leu Arg Tyr Ser Trp Lys Thr Trp Gly Lys Ala
            885                 890                 895 aaa atg ctc tcc aca gaa ctc cat aat cag acc ttc ctc att gat ggt    2736
Lys Met Leu Ser Thr Glu Leu His Asn Gln Thr Phe Leu Ile Asp Gly
        900                 905                 910 ccc gaa aca gca gaa tgc ccc aac aca aac aga gct tgg aat tca cta    2784
Pro Glu Thr Ala Glu Cys Pro Asn Thr Asn Arg Ala Trp Asn Ser Leu
    915                 920                 925 gaa gtt gag gac tac ggc ttt gga gta ttc act acc aat ata tgg cta    2832
Glu Val Glu Asp Tyr Gly Phe Gly Val Phe Thr Thr Asn Ile Trp Leu
930                 935                 940 aga ttg aga gaa aag cag gat gca ttt tgt gac tca aaa ctc atg tca    2880
Arg Leu Arg Glu Lys Gln Asp Ala Phe Cys Asp Ser Lys Leu Met Ser
945                 950                 955                 960 gcg gcc ata aag gac aac aga gcc gtc cat gct gat atg ggt tat tgg    2928
Ala Ala Ile Lys Asp Asn Arg Ala Val His Ala Asp Met Gly Tyr Trp
                965                 970                 975 ata gaa agc gca ctc aat gat aca tgg aag ata gag aaa gct tct ttc    2976
Ile Glu Ser Ala Leu Asn Asp Thr Trp Lys Ile Glu Lys Ala Ser Phe
            980                 985                 990 att gaa gtc aaa agt tgc cac tgg cca aag tca cac act cta tgg agt    3024
Ile Glu Val Lys Ser Cys His Trp Pro Lys Ser His Thr Leu Trp Ser
        995                 1000                1005 aat gga gtg cta gaa agc gag atg gta att cca aag aat ttc gct gga    3072
Asn Gly Val Leu Glu Ser Glu Met Val Ile Pro Lys Asn Phe Ala Gly
    1010                1015                1020 cca gtg tca caa cat aat aac aga cca ggc tat cac aca caa aca gca    3120
Pro Val Ser Gln His Asn Asn Arg Pro Gly Tyr His Thr Gln Thr Ala
1025                1030                1035                1040 gga cct tgg cat cta ggc aag ctt gag atg gac ttt gat ttc tgc gaa    3168
Gly Pro Trp His Leu Gly Lys Leu Glu Met Asp Phe Asp Phe Cys Glu
                1045                1050                1055 ggg act aca gtg gtg gta acc gag gac tgt gga aac aga ggg ccc tct    3216
Gly Thr Thr Val Val Val Thr Glu Asp Cys Gly Asn Arg Gly Pro Ser
            1060                1065                1070 tta aga aca acc act gcc tca gga aaa ctc ata acg gaa tgg tgt tgt    3264
Leu Arg Thr Thr Thr Ala Ser Gly Lys Leu Ile Thr Glu Trp Cys Cys
        1075                1080                1085 cga tct tgc aca cta cca cca cta aga tac aga ggt gag gat gga tgc    3312
Arg Ser Cys Thr Leu Pro Pro Leu Arg Tyr Arg Gly Glu Asp Gly Cys
    1090                1095                1100 tgg tac ggg atg gaa atc aga cca ttg aaa gag aaa gaa gaa aat ctg    3360
Trp Tyr Gly Met Glu Ile Arg Pro Leu Lys Glu Lys Glu Glu Asn Leu
1105                1110                1115                1120 gtc agt tct ctg gtc aca gcc                                        3381
Val Ser Ser Leu Val Thr Ala
                1125

<210> SEQ ID NO 3
<211> LENGTH: 1127
<212> TYPE: PRT
<213> ORGANISM: Dengue virus

<400> SEQUENCE: 3

Met Asn Asn Gln Arg Lys Lys Ala Arg Asn Thr Pro Phe Asn Met Leu
1               5                   10                  15
```

-continued

```
Lys Arg Glu Arg Asn Arg Val Ser Thr Val Gln Gln Leu Thr Lys Arg
             20                  25                  30
Phe Ser Leu Gly Met Leu Gln Gly Arg Gly Pro Leu Lys Leu Phe Met
         35                  40                  45
Ala Leu Val Ala Phe Leu Arg Phe Leu Thr Ile Pro Pro Thr Ala Gly
 50                  55                  60
Ile Leu Lys Arg Trp Gly Thr Ile Lys Lys Ser Lys Ala Ile Asn Val
 65                  70                  75                  80
Leu Arg Gly Phe Arg Lys Glu Ile Gly Arg Met Leu Asn Ile Leu Asn
                 85                  90                  95
Arg Arg Arg Arg Thr Ala Gly Met Ile Ile Met Leu Ile Pro Thr Val
                100                 105                 110
Met Ala Phe His Leu Thr Thr Arg Asn Gly Glu Pro His Met Ile Val
            115                 120                 125
Ser Arg Gln Glu Lys Gly Lys Ser Leu Leu Phe Lys Thr Lys Asp Gly
        130                 135                 140
Thr Asn Met Cys Thr Leu Met Ala Met Asp Leu Gly Glu Leu Cys Glu
145                 150                 155                 160
Asp Thr Ile Thr Tyr Lys Cys Pro Phe Leu Lys Gln Asn Glu Pro Glu
                165                 170                 175
Asp Ile Asp Cys Trp Cys Asn Ser Thr Ser Thr Trp Val Thr Tyr Gly
                180                 185                 190
Thr Cys Thr Thr Thr Gly Glu His Arg Arg Glu Lys Arg Ser Val Ala
            195                 200                 205
Leu Val Pro His Val Gly Met Gly Leu Glu Thr Arg Thr Glu Thr Trp
        210                 215                 220
Met Ser Ser Glu Gly Ala Trp Lys His Ala Gln Arg Ile Glu Thr Trp
225                 230                 235                 240
Ile Leu Arg His Pro Gly Phe Thr Ile Met Ala Ala Ile Leu Ala Tyr
                245                 250                 255
Thr Ile Gly Thr Thr His Phe Gln Arg Val Leu Ile Phe Ile Leu Leu
                260                 265                 270
Thr Ala Ile Ala Pro Ser Met Thr Met Arg Cys Ile Gly Ile Ser Asn
        275                 280                 285
Arg Asp Phe Val Glu Gly Val Ser Gly Gly Ser Trp Val Asp Ile Val
290                 295                 300
Leu Glu His Gly Ser Cys Val Thr Thr Met Ala Lys Asn Lys Pro Thr
305                 310                 315                 320
Leu Asp Phe Glu Leu Ile Lys Thr Glu Ala Lys Gln Pro Ala Thr Leu
                325                 330                 335
Arg Lys Tyr Cys Ile Glu Ala Lys Leu Thr Asn Thr Thr Asp Ser
                340                 345                 350
Arg Cys Pro Thr Gln Gly Glu Pro Thr Leu Asn Glu Glu Gln Asp Lys
        355                 360                 365
Arg Phe Val Cys Lys His Ser Met Val Asp Arg Gly Trp Gly Asn Gly
        370                 375                 380
Cys Gly Leu Phe Gly Lys Gly Gly Ile Val Thr Cys Ala Met Phe Thr
385                 390                 395                 400
Cys Lys Lys Asn Met Glu Gly Lys Ile Val Gln Pro Glu Asn Leu Glu
                405                 410                 415
Tyr Thr Val Val Ile Thr Pro His Ser Gly Glu Glu His Ala Val Gly
                420                 425                 430
Asn Asp Thr Gly Lys His Gly Lys Glu Val Lys Ile Thr Pro Gln Ser
```

-continued

```
                435                 440                 445
Ser Ile Thr Glu Ala Glu Leu Thr Gly Tyr Gly Thr Val Thr Met Glu
450                 455                 460

Cys Ser Pro Arg Thr Gly Leu Asp Phe Asn Glu Met Val Leu Leu Gln
465                 470                 475                 480

Met Lys Asp Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Leu Gly Ser Gln Gly Ala Met His Thr Ala Leu
530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
                580                 585                 590

Ala Glu Thr Gln His Gly Thr Ile Val Ile Arg Val Gln Tyr Glu Gly
            595                 600                 605

Asp Gly Ser Pro Cys Lys Ile Pro Phe Glu Ile Met Asp Leu Glu Lys
        610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Gly Val Glu Pro Gly Gln Leu Lys Leu Asp Trp Phe
                660                 665                 670

Lys Lys Gly Ser Ser Ile Gly Gln Met Phe Glu Thr Thr Met Arg Gly
            675                 680                 685

Ala Lys Arg Met Ala Ile Leu Gly Asp Thr Ala Trp Asp Phe Gly Ser
        690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
                740                 745                 750

Thr Ser Leu Ser Val Ser Leu Val Leu Val Gly Ile Val Thr Leu Tyr
            755                 760                 765

Leu Gly Val Met Val Gln Ala Asp Ser Gly Cys Val Val Ser Trp Lys
        770                 775                 780

Asn Lys Glu Leu Lys Cys Gly Ser Gly Ile Phe Val Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Gly Ile Cys Gly Ile
            820                 825                 830

Arg Ser Val Thr Arg Leu Glu Asn Leu Met Trp Lys Gln Ile Thr Ser
        835                 840                 845

Glu Leu Asn His Ile Leu Ser Glu Asn Glu Val Lys Leu Thr Ile Met
850                 855                 860
```

```
Thr Gly Asp Ile Lys Gly Ile Met Gln Val Gly Lys Arg Ser Leu Arg
865                 870                 875                 880

Pro Gln Pro Thr Glu Leu Arg Tyr Ser Trp Lys Thr Trp Gly Lys Ala
            885                 890                 895

Lys Met Leu Ser Thr Glu Leu His Asn Gln Thr Phe Leu Ile Asp Gly
        900                 905                 910

Pro Glu Thr Ala Glu Cys Pro Asn Thr Asn Arg Ala Trp Asn Ser Leu
    915                 920                 925

Glu Val Glu Asp Tyr Gly Phe Gly Val Phe Thr Thr Asn Ile Trp Leu
        930                 935                 940

Arg Leu Arg Glu Lys Gln Asp Ala Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Ser Cys His Trp Pro Lys Ser His Thr Leu Trp Ser
        995                 1000                1005

Asn Gly Val Leu Glu Ser Glu Met Val Ile Pro Lys Asn Phe Ala Gly
    1010                1015                1020

Pro Val Ser Gln His Asn Asn Arg Pro Gly Tyr His Thr Gln Thr Ala
1025                1030                1035                1040

Gly Pro Trp His Leu Gly Lys Leu Glu Met Asp Phe Asp Phe Cys Glu
                1045                1050                1055

Gly Thr Thr Val Val Val Thr Glu Asp Cys Gly Asn Arg Gly Pro Ser
            1060                1065                1070

Leu Arg Thr Thr Thr Ala Ser Gly Lys Leu Ile Thr Glu Trp Cys Cys
        1075                1080                1085

Arg Ser Cys Thr Leu Pro Pro Leu Arg Tyr Arg Gly Glu Asp Gly Cys
    1090                1095                1100

Trp Tyr Gly Met Glu Ile Arg Pro Leu Lys Glu Lys Glu Glu Asn Leu
1105                1110                1115                1120

Val Ser Ser Leu Val Thr Ala
                1125

<210> SEQ ID NO 4
<211> LENGTH: 25
<212> TYPE: PRT
<213> ORGANISM: Artificial sequence
<220> FEATURE:
<223> OTHER INFORMATION: Linked 80%E dimer

<400> SEQUENCE: 4

Gly Gly Gly Ser Gly Gly Gly Ser Gly Gly Thr Gly Gly
 1               5                  10                  15

Ser Gly Gly Gly Ser Gly Gly Gly Gly
            20                  25

<210> SEQ ID NO 5
<211> LENGTH: 55
<212> TYPE: PRT
<213> ORGANISM: Artificial Sequence
<220> FEATURE:
<223> OTHER INFORMATION: 80%E ZipperI

<400> SEQUENCE: 5

Gly Gly Gly Ser Gly Gly Gly Ser Gly Gly Thr Gly Gly Gly
```

```
                1               5                  10                 15
Ser Gly Gly Gly Ser Pro Arg Met Lys Gln Leu Glu Asp Lys Val Glu
                    20                  25                  30

Glu Leu Leu Ser Lys Asn Tyr His Leu Glu Asn Glu Val Ala Arg Leu
            35                  40                  45

Lys Lys Leu Val Gly Glu Arg
    50                  55
```

<210> SEQ ID NO 6
<211> LENGTH: 60
<212> TYPE: PRT
<213> ORGANISM: Artificial Sequence
<220> FEATURE:
<223> OTHER INFORMATION: 80%E ZipperII

<400> SEQUENCE: 6

```
Gly Gly Gly Ser Gly Gly Gly Ser Gly Gly Thr Gly Gly Gly
  1               5                  10                 15

Ser Gly Gly Ser Pro Arg Met Lys Gln Leu Glu Asp Lys Val Glu
                    20                  25                  30

Glu Leu Leu Ser Lys Asn Tyr His Leu Glu Asn Glu Val Ala Arg Leu
            35                  40                  45

Lys Lys Leu Val Gly Glu Arg Gly Gly Cys Gly Gly
    50                  55                  60
```

<210> SEQ ID NO 7
<211> LENGTH: 5
<212> TYPE: PRT
<213> ORGANISM: Artificial Sequence
<220> FEATURE:
<223> OTHER INFORMATION: End of 80%E ZipperII domain

<400> SEQUENCE: 7

```
Gly Gly Cys Gly Gly
  1               5
```

<210> SEQ ID NO 8
<211> LENGTH: 59
<212> TYPE: PRT
<213> ORGANISM: Artificial Sequence
<220> FEATURE:
<223> OTHER INFORMATION: 80%E Bundle

<400> SEQUENCE: 8

```
Gly Gly Gly Ser Gly Gly Gly Ser Gly Gly Thr Gly Gly Gly
  1               5                  10                 15

Ser Gly Gly Ser Pro Gly Glu Leu Glu Glu Leu Leu Lys His Leu
                    20                  25                  30

Lys Glu Leu Leu Lys Gly Pro Arg Lys Gly Glu Leu Glu Glu Leu Leu
            35                  40                  45

Lys His Leu Lys Glu Leu Leu Lys Gly Glu Phe
    50                  55
```

<210> SEQ ID NO 9
<211> LENGTH: 46
<212> TYPE: DNA
<213> ORGANISM: Artificial Sequence
<220> FEATURE:
<223> OTHER INFORMATION: Primer

<400> SEQUENCE: 9
cttctagatc tcgagtaccc gggacc atg cgc tgc ata gga ata tc        46

<210> SEQ ID NO 10
<211> LENGTH: 6
<212> TYPE: PRT
<213> ORGANISM: Artificial Sequence
<220> FEATURE:
<223> OTHER INFORMATION: Primer encoded amino acid sequence

<400> SEQUENCE: 10

Met Arg Cys Ile Gly Ile
1               5

<210> SEQ ID NO 11
<211> LENGTH: 35
<212> TYPE: DNA
<213> ORGANISM: Artificial Sequence
<220> FEATURE:
<223> OTHER INFORMATION: Primer

<400> SEQUENCE: 11
gctctagagt cgactattat cctttcttga accag                          35

<210> SEQ ID NO 12
<211> LENGTH: 5
<212> TYPE: PRT
<213> ORGANISM: Artificial Sequence
<220> FEATURE:
<223> OTHER INFORMATION: Primer encoded amino acid sequence

<400> SEQUENCE: 12

Gly Lys Lys Phe Trp
1               5

<210> SEQ ID NO 13
<211> LENGTH: 47
<212> TYPE: DNA
<213> ORGANISM: Artificial Sequence
<220> FEATURE:
<223> OTHER INFORMATION: Primer

<400> SEQUENCE: 13
attctagatc tcgagtaccc gggacc atg ttt cat ctg acc aca cgc        47

<210> SEQ ID NO 14
<211> LENGTH: 7
<212> TYPE: PRT
<213> ORGANISM: Artificial Sequence
<220> FEATURE:
<223> OTHER INFORMATION: Primer encoded amino acid sequence

<400> SEQUENCE: 14

Met Phe His Leu Thr Thr Arg
1               5

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
tctctagagt cgactattag gcctgcacca taactcc                        37

<210> SEQ ID NO 16
<211> LENGTH: 6

```
<212> TYPE: PRT
<213> ORGANISM: Artificial Sequence
<220> FEATURE:
<223> OTHER INFORMATION: Primer encoded amino acid sequence

<400> SEQUENCE: 16

Ala Gln Val Met Val Gly
 1               5

<210> SEQ ID NO 17
<211> LENGTH: 78
<212> TYPE: DNA
<213> ORGANISM: Artificial Sequence
<220> FEATURE:
<223> OTHER INFORMATION: Primer

<400> SEQUENCE: 17
agtcctgcag gt acc ggt ggt ggt ggt tct ggt ggt ggt tct ggt ggt ggt    51 atg cgt tgc ata gga ata tca aat agg                                  78

<210> SEQ ID NO 18
<211> LENGTH: 22
<212> TYPE: PRT
<213> ORGANISM: Artificial Sequence
<220> FEATURE:
<223> OTHER INFORMATION: Primer encoded amino acid sequence

<400> SEQUENCE: 18

Thr Gly Gly Gly Gly Ser Gly Gly Gly Ser Gly Gly Gly Met Arg Cys
 1               5                  10                  15

Ile Gly Ile Ser Asn Arg
             20

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
ctatgatgat gtagctgtct cc                                             22

<210> SEQ ID NO 20
<211> LENGTH: 7
<212> TYPE: PRT
<213> ORGANISM: Artificial Sequence
<220> FEATURE:
<223> OTHER INFORMATION: Primer

<400> SEQUENCE: 20

Ile Ile Ile Tyr Ser Asp Gly
 1               5

<210> SEQ ID NO 21
<211> LENGTH: 72
<212> TYPE: DNA
<213> ORGANISM: Artificial Sequence
<220> FEATURE:
<223> OTHER INFORMATION: Primer

<400> SEQUENCE: 21
gctcagctgc aggtaccacc accagaacca ccaccaccag aaccaccacc acctttcttg    60
aaccagtcca gc                                                        72
```

<210> SEQ ID NO 22
<211> LENGTH: 19
<212> TYPE: PRT
<213> ORGANISM: Artificial Sequence
<220> FEATURE:
<223> OTHER INFORMATION: Primer

<400> SEQUENCE: 22

Gly Gly Gly Ser Gly Gly Gly Ser Gly Gly Gly Lys Lys Phe
 1               5                  10                  15
Trp Asp Leu

<210> SEQ ID NO 23
<211> LENGTH: 15
<212> TYPE: DNA
<213> ORGANISM: Artificial Sequence
<220> FEATURE:
<223> OTHER INFORMATION: Primer

<400> SEQUENCE: 23
gacactggtc acctt                                                      15

<210> SEQ ID NO 24
<211> LENGTH: 5
<212> TYPE: PRT
<213> ORGANISM: Artificial Sequence
<220> FEATURE:
<223> OTHER INFORMATION: Primer

<400> SEQUENCE: 24

Thr Leu Val Thr Phe
 1               5

<210> SEQ ID NO 25
<211> LENGTH: 138
<212> TYPE: DNA
<213> ORGANISM: Artificial Sequence
<220> FEATURE:
<223> OTHER INFORMATION: Resulting plasmid

<400> SEQUENCE: 25 gt acc ggc ggt ggc tcc ggc ggt ggc tcc ccc cgc atg aag cag ctg        47 gag gac aag gtg gag gag ctg ctg tcc aag aac tac cac ctg gag aac       95 gag gtg gcc cgc ctg aag aag ctg gtg ggc gag cgc taatagg              138

<210> SEQ ID NO 26
<211> LENGTH: 43
<212> TYPE: PRT
<213> ORGANISM: Artificial Sequence
<220> FEATURE:
<223> OTHER INFORMATION: Plasmid encoded amino acid sequence

<400> SEQUENCE: 26

Thr Gly Gly Gly Ser Gly Gly Gly Ser Pro Arg Met Lys Gln Leu Glu
 1               5                  10                  15
Asp Lys Val Glu Glu Leu Leu Ser Lys Asn Tyr His Leu Glu Asn Glu
                20                  25                  30
Val Ala Arg Leu Lys Lys Leu Val Gly Glu Arg
                35                  40

<210> SEQ ID NO 27
<211> LENGTH: 138
<212> TYPE: DNA

```
<213> ORGANISM: Artificial Sequence
<220> FEATURE:
<223> OTHER INFORMATION: Resulting plasmid (complementary chain)

<400> SEQUENCE: 27
tcgacctatt agcgctcgcc caccagcttc ttcaggcggg ccacctcgtt ctccaggtgg      60
tagttcttgg acagcagctc ctccaccttg tcctccagct gcttcatgcg ggggagcca     120 ccgccggagc caccgccg                                                    138

<210> SEQ ID NO 28
<211> LENGTH: 153
<212> TYPE: DNA
<213> ORGANISM: Artificial Sequence
<220> FEATURE:
<223> OTHER INFORMATION: Resulting plasmid

<400> SEQUENCE: 28 gt acc ggc ggt ggc tcc ggc ggt ggc tcc ccc cgc atg aag cag ctg        47 gag gac aag gtg gag gag ctg ctg tcc aag aac tac cac ctg gag aac       95 gag gtg gcc cgc ctg aag aag ctg gtg ggc gag cgc ggc ggt tgc ggc      143 ggt taatagg                                                           153

<210> SEQ ID NO 29
<211> LENGTH: 48
<212> TYPE: PRT
<213> ORGANISM: Artificial Sequence
<220> FEATURE:
<223> OTHER INFORMATION: Plasmid encoded amino acid sequence

<400> SEQUENCE: 29

Thr Gly Gly Gly Ser Gly Gly Gly Ser Pro Arg Met Lys Gln Leu Glu
  1               5                  10                  15

Asp Lys Val Glu Glu Leu Leu Ser Lys Asn Tyr His Leu Glu Asn Glu
                 20                  25                  30

Val Ala Arg Leu Lys Lys Leu Val Gly Glu Arg Gly Gly Cys Gly Gly
             35                  40                  45

<210> SEQ ID NO 30
<211> LENGTH: 153
<212> TYPE: DNA
<213> ORGANISM: Artificial Sequence
<220> FEATURE:
<223> OTHER INFORMATION: Resulting plasmid (complementary chain)

<400> SEQUENCE: 30
tcgacctatt aaccgccgca accgccgcgc tcgcccacca gcttcttcag gcgggccacc      60
tcgttctcca ggtggtagtt cttggacagc agctcctcca ccttgtcctc cagctgcttc    120
atgcgggggg agccaccgcc ggagccaccg ccg                                  153

<210> SEQ ID NO 31
<211> LENGTH: 150
<212> TYPE: DNA
<213> ORGANISM: Artificial Sequence
<220> FEATURE:
<223> OTHER INFORMATION: Resulting plasmid

<400> SEQUENCE: 31 gt acc ggc ggt ggc tcc ggc ggt ggc tcc ccc ggc gag ctg gag gag        47 ctg ctg aag cac ctg aag gag ctg ctg aag ggc ccc cgc aag ggc gag       95
``` ctg gag gag ctg ctg aag cac ctg aag gag ctg ctg aag ggc gag ttc    143 taatagg    150

<210> SEQ ID NO 32
<211> LENGTH: 47
<212> TYPE: PRT
<213> ORGANISM: Artificial Sequence
<220> FEATURE:
<223> OTHER INFORMATION: Plasmid encoded amino acid sequence

<400> SEQUENCE: 32

Thr Gly Gly Gly Ser Gly Gly Gly Ser Pro Gly Glu Leu Glu Glu Leu
 1               5                  10                  15

Leu Lys His Leu Lys Glu Leu Leu Lys Gly Pro Arg Lys Gly Glu Leu
            20                  25                  30

Glu Glu Leu Leu Lys His Leu Lys Glu Leu Leu Lys Gly Glu Phe
        35                  40                  45

<210> SEQ ID NO 33
<211> LENGTH: 150
<212> TYPE: DNA
<213> ORGANISM: Artificial Sequence
<220> FEATURE:
<223> OTHER INFORMATION: Resulting plasmid (complementary chain)

<400> SEQUENCE: 33
tcgacctatt agaactcgcc cttcagcagc tccttcaggt gcttcagcag ctcctccagc    60
tcgcccttgc gggggccctt cagcagctcc ttcaggtgct tcagcagctc ctccagctcg    120 ccggggagc accgccgga gccaccgccg    150

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
ccaggtcacc atgggtag    18

<210> SEQ ID NO 35
<211> LENGTH: 47
<212> TYPE: DNA
<213> ORGANISM: Artificial Sequence
<220> FEATURE:
<223> OTHER INFORMATION: Primer

<400> SEQUENCE: 35
accaccacca ccagaaccac cacccccttt cctgaaccaa tggagtg    47

<210> SEQ ID NO 36
<211> LENGTH: 50
<212> TYPE: DNA
<213> ORGANISM: Artificial Sequence
<220> FEATURE:
<223> OTHER INFORMATION: Positive strand primer

<400> SEQUENCE: 36
tcaggaaagg gggtggtggt tctggtggtg gtggttctgg tggtggtacc    50

<210> SEQ ID NO 37
<211> LENGTH: 20
<212> TYPE: DNA

```
<213> ORGANISM: Artificial Sequence
<220> FEATURE:
<223> OTHER INFORMATION: Negative strand primer

<400> SEQUENCE: 37
ataccgcaag cgacaggccg                                              20
```